United States Patent
Iida et al.

(10) Patent No.: US 12,265,039 B2
(45) Date of Patent: Apr. 1, 2025

(54) MEASUREMENT DEVICE, MEASUREMENT SYSTEM, AND MEASUREMENT METHOD

(71) Applicant: SONY GROUP CORPORATION, Tokyo (JP)

(72) Inventors: Sachio Iida, Chiba (JP); Atsushi Yamada, Kanagawa (JP); Takuya Ichihara, Tokyo (JP); Toshiyuki Hiroi, Tokyo (JP)

(73) Assignee: Sony Group Corporation, Tokyo (JP)

( * ) Notice: Subject to any disclaimer, the term of this patent is extended or adjusted under 35 U.S.C. 154(b) by 378 days.

(21) Appl. No.: 17/609,206

(22) PCT Filed: May 7, 2020

(86) PCT No.: PCT/JP2020/018574
§ 371 (c)(1),
(2) Date: Nov. 5, 2021

(87) PCT Pub. No.: WO2020/230702
PCT Pub. Date: Nov. 19, 2020

(65) Prior Publication Data
US 2022/0205931 A1  Jun. 30, 2022

(30) Foreign Application Priority Data

May 13, 2019 (JP) .................. 2019-090371
Apr. 24, 2020 (JP) .................. 2020-077039

(51) Int. Cl.
*G01N 22/04* (2006.01)
*G01N 33/24* (2006.01)

(52) U.S. Cl.
CPC ........... *G01N 22/04* (2013.01); *G01N 33/246* (2013.01)

(58) Field of Classification Search
CPC .............................. G01N 22/04; G01N 33/246
See application file for complete search history.

(56) References Cited

U.S. PATENT DOCUMENTS

| 4,361,801 A | 11/1982 | Meyer et al. |
| 5,633,709 A * | 5/1997 | Ohtaki ............... G01R 27/04 356/73.1 |

(Continued)

FOREIGN PATENT DOCUMENTS

| CN | 104377445 A * | 2/2015 |
| JP | S56-019443 | 2/1981 |

(Continued)

OTHER PUBLICATIONS

Written Opinion of the International Searching Authority, PCT/JP2020/018574, Nov. 13, 2021 (Year: 2021).*

(Continued)

*Primary Examiner* — Vladimir Magloire
*Assistant Examiner* — Noah Yi Min Zhu
(74) *Attorney, Agent, or Firm* — SHERIDAN ROSS P.C.

(57) ABSTRACT

A measurement device that measures an amount of moisture in a medium. The device includes a transmitter that transmits an electrical signal including an incident wave to one of a pair of probes in which a cable has been embedded through the cable. A receiver receives a reflected wave obtained from reflection of the incident wave by the one of the pairs of probes and a transmitted wave that has been transmitted through a medium between the pair of probes through the cable. A processing unit obtains a reciprocating delay time corresponding to a time over which the electrical signal reciprocates through the cable and measures an amount of moisture contained in the medium on the basis of the reciprocating delay time and a propagation transmission time corresponding to a time over which electromagnetic waves propagate and the electrical signal is transmitted through the medium and the cable.

19 Claims, 21 Drawing Sheets

(56) References Cited

U.S. PATENT DOCUMENTS

| | | | |
|---|---|---|---|
| 5,646,537 A | 7/1997 | Skaling et al. | |
| 6,147,503 A | 11/2000 | Nelson et al. | |
| 7,112,971 B2 * | 9/2006 | Kohler | G01N 22/04 |
| | | | 324/637 |
| 8,742,768 B1 | 6/2014 | Pelletier | |
| 10,073,074 B1 * | 9/2018 | Kumar | G01N 27/026 |
| 2003/0118832 A1 * | 6/2003 | Skaling | G01N 33/246 |
| | | | 428/413 |
| 2005/0150278 A1 | 7/2005 | Troxler et al. | |
| 2007/0188177 A1 | 8/2007 | Troxler et al. | |
| 2014/0009170 A1 | 1/2014 | Troxler et al. | |
| 2015/0028890 A1 | 1/2015 | Troxler et al. | |
| 2017/0077587 A1 * | 3/2017 | Fleancu | H01Q 1/20 |
| 2020/0196248 A1 * | 6/2020 | Kerger | H04W 52/283 |
| 2020/0292472 A1 * | 9/2020 | Wolleben | G01V 3/08 |

FOREIGN PATENT DOCUMENTS

| | | |
|---|---|---|
| JP | H11-173998 | 7/1999 |
| JP | 2000-146867 | 5/2000 |
| JP | 2000-258360 | 9/2000 |
| JP | 2002-174666 | 6/2002 |
| JP | 2006-133088 | 5/2006 |
| JP | 2011-027664 | 2/2011 |
| JP | 2011-191208 | 9/2011 |
| JP | 2012-194027 | 10/2012 |
| JP | 2018-207403 | 12/2018 |
| JP | 2018207403 A * | 12/2018 |
| WO | WO 2005/043142 | 5/2005 |
| WO | WO-2017021950 A | 2/2017 |
| WO | WO 2018/221051 | 12/2018 |
| WO | WO-2018221051 A1 * | 12/2018 ............ G01N 22/04 |

OTHER PUBLICATIONS

"Study on applicability of measuring method of salt content in reinforced concrete by electromagnetic wave to the actual structure," Proceedings of the Japan Concrete Institute, vol. 26, No. 1, Jan. 2004, pp. 1869-1874 (no English translation available).

Hossain, "Transmission and permeation of wave groups by the composite breakwater," Proceedings of Coastal Engineering, JSCE, vol. 47, Oct. 20, 2000, pp. 721-725 (no English translation available).

Maruyama et al., "Measurement of Water Content in Hardened Cement Paste Using Terahertz Radiation," Journal of Structural and Construction Engineering, vol. 75, No. 652, Jun. 2010, pp. 1073-1079 (no English translation available).

International Search Report prepared by the Japan Patent Office on Aug. 3, 2020, for International Application No. PCT/JP2020/018574, 4 pgs.

* cited by examiner a b

MEASUREMENT DEVICE, MEASUREMENT SYSTEM, AND MEASUREMENT METHOD

CROSS REFERENCE TO RELATED APPLICATIONS

This application is a national stage application under 35 U.S.C. 371 and claims the benefit of PCT Application No. PCT/JP2020/018574 having an international filing date of 7 May 2020, which designated the United States, which PCT application claimed the benefit of Japanese Patent Application Nos. 2019-090371 filed 13 May 2019, and 2020-077039 filed 24 Apr. 2020, the entire disclosures of each of which are incorporated herein by reference.

TECHNICAL FIELD

The present technology relates to a measurement device, a measurement system, and a measurement method. Specifically, the present technology relates to a measurement device in which a pair of probes is provided, a measurement system, and a measurement method.

BACKGROUND ART

Conventionally, devices and apparatuses for measuring the amount of moisture in a medium such as soil are widely used in fields such as agriculture and environmental investigation. For example, a sensor device that measures the amount of moisture from a propagation delay time over which electromagnetic waves propagate through a medium between a pair of probes is proposed (refer to PTL 1, for example). This sensor device connects the pair of probes to a transmitter and a receiver through a cable, transmits an electrical signal from the transmitter to the receiver, and obtains a delay time from transmission to reception. Then, the sensor device having stored a transmission time over which the electrical signal is transmitted through the cable as an error of a fixed value in advance subtracts the error from the obtained delay time to obtain a propagation delay time over which electromagnetic waves propagate through a medium.

CITATION LIST

Patent Literature

[PTL 1]
WO 2018/221051

SUMMARY

Technical Problem

In the aforementioned sensor device, improvement in accuracy of measurement of the amount of moisture is promoted by subtracting the error at the time of obtaining the propagation delay time of the electromagnetic waves. However, the length of the cable may change due to thermal expansion and the error may also change caused by this change in the length. Accordingly, in the aforementioned sensor device in which the error is set as a fixed value, accuracy of measurement of the amount of moisture may deteriorate when the cable has thermally expanded.

The present technology has been made in view of such a situation, and an object of the present technology is to improve accuracy of measurement of an amount of moisture in a measurement device that measures an amount of moisture in a medium.

Solution to Problem

The present technology is devised to solve the above-described problems and a first aspect thereof is a measurement device including; a transmitter configured to transmit an electrical signal including an incident wave to one of a pair of probes in which a cable has been embedded through the cable; a receiver configured to receive a reflected wave obtained from reflection of the incident light by the one of the pair of probes and a transmitted wave that has been transmitted through a medium between the pair of probes through the cable; and a processing unit configured to obtain a reciprocating delay time corresponding to a time over which the electrical signal reciprocates through the cable and to measure an amount of moisture contained in the medium on the basis of the reciprocating delay time and a propagation transmission time corresponding to a time over which electromagnetic waves propagate and the electrical signal is transmitted through the medium and the cable, and a measurement method thereof. Accordingly, the amount of moisture is measured from the reciprocating delay time and the propagation transmission time.

Further, in the first aspect, an outer shell configured to isolate the pair of probes from the medium may be further included. Accordingly, the reciprocating delay time becomes constant irrespective of the amount of moisture.

Further, in the first aspect, the outer shell may be formed of an electromagnetic wave transmitting material. Accordingly, electromagnetic waves are transmitted through the outer shell.

Further, in the first aspect, a spacer configured to keep a constant interval between the pair of probes can be further included. Accordingly, an interval between the probes is defined.

Further, in the first aspect, the spacer may be formed of an electromagnetic wave transmitting material. Accordingly, electromagnetic waves are transmitted through the spacer.

Further, in the first aspect, an outer edge of the spacer which is close to antenna parts of the pair of probes between outer edges extending between the pair of probes may have an arc shape Accordingly, noise is reduced.

In addition, in the first aspect, a distance from the antenna parts of the pair of probes to a lower end of the spacer may be greater than an inter-antenna distance corresponding to a distance between the antenna parts, desirably, greater than twice the inter-antenna distance, more desirably, greater than three times the inter-antenna distance, and less than a length of the probes. Accordingly, noise is reduced.

In addition, in the first aspect, a controller configured to perform control for causing the incident wave to be transmitted, processing of obtaining a ratio between complex amplitudes of the incident wave and the reflected wave as a reflection coefficient, and processing of obtaining a ratio between complex amplitudes of the incident wave and the transmitted wave as a transmission coefficient may be further included, wherein the processing unit may obtain the reciprocating delay time and the propagation transmission time on the basis of the reflection coefficient and the transmission coefficient. Accordingly, the amount of moisture is measured on the basis of the reciprocating delay time and the propagation transmission time obtained from the reflection coefficient and the transmission coefficient.

Further, in the first aspect, the controller and the processing unit may be provided in a predetermined semiconductor chip. Accordingly, the number of chips of the measurement device is reduced.

Further, in the first aspect, the controller may be provided in a predetermined semiconductor chip, and the processing unit may be provided in a semiconductor chip different from the semiconductor chip. Accordingly, an amount of moisture is measured in a measurement device in which a plurality of semiconductor chips are provided.

Further, in the first aspect, a communication unit configured to wirelessly transmit the reflection coefficient and the transmission coefficient to the processing unit may be further included. Accordingly, the amount of moisture may be measured even if the processing unit is disposed at a remote place.

Further, in the first aspect, a directional coupler configured to separate an electrical signal transmitted through the cable into the incident wave and the reflected wave may be further included. Accordingly, the separated incident wave and reflected wave are respectively received.

Further, in the first aspect, the receiver may include an incident wave receiver configured to receive the incident wave, a reflected wave receiver configured to receive the reflected wave, and a transmitted wave receiver configured to receive the transmitted wave. Accordingly, the incident wave, the reflected wave, and the transmitted wave are respectively received.

Further, in the first aspect, the incident wave may include first and second incident waves in different directions, the reflected wave may include a first reflected wave corresponding to the first incident wave and a second reflected wave corresponding to the second incident wave, the transmitted wave may include a second transmitted wave corresponding to the first incident wave and a first transmitted wave corresponding to the second incident wave, the directional coupler may include a first directional coupler configured to separate the electrical signal into the first incident wave and the first reflected wave and a second directional coupler configured to separate the electrical signal into the second incident wave and the second reflected wave, the transmitter may include a first transmitter configured to transmit the first incident wave and a second transmitter configured to transmit the second incident wave, and the receiver may include a first receiver configured to sequentially receive the first reflected wave and the first transmitted wave and a second receiver configured to sequentially receive the second reflected wave and the second transmitted wave. Accordingly, the first and second incident waves in different directions, and the reflected waves and the transmitted waves corresponding thereto are received.

Further, in the first aspect, the reciprocating delay time may include a first reciprocating delay time corresponding to one of the pair of probes and a second reciprocating delay time corresponding to the other of the pair of probes, and the processing unit may obtain the first reciprocating delay time from the first incident wave and the first reflected wave and obtain the second reciprocating delay time from the second incident wave and the second reflected wave. Accordingly, a reciprocating delay time corresponding to each of the pair of probes is acquired.

Further, in the first aspect, the processing unit may obtain a propagation delay time corresponding to a time over which the electromagnetic waves propagate through the medium from the reciprocating delay time and the propagation transmission time and measure an amount of moisture according to the propagation delay time. Accordingly, the amount of moisture according to the propagation delay time is measured.

Further, in the first aspect, the processing unit may store a predetermined coefficient representing a relationship between the propagation delay time and the amount of moisture and measure the amount of moisture from the obtained propagation delay time and the coefficient. Accordingly, the amount of moisture is measured from the propagation delay time and the coefficient.

In addition, a second aspect of the present technology is a measurement system including: a transmitter configured to transmit an electrical signal including an incident wave to one of a pair of probes to which a cable has been connected through the cable; a receiver configured to receive a reflected wave obtained from reflection of the incident light by the one of the pair of probes and a transmitted wave that has been transmitted through a medium between the pair of probes through the cable; a controller configured to perform control for causing the incident wave to be transmitted and processing of obtaining a ratio between complex amplitudes of the incident wave and the reflected wave as a reflection coefficient; and a processing unit configured to obtain a reciprocating delay time corresponding to a time over which the electrical signal reciprocates through the cable from the reflection coefficient and to measure an amount of moisture contained in the medium on the basis of the reciprocating delay time and a propagation transmission time corresponding to a time over which electromagnetic waves propagate and the electrical signal is transmitted through the medium and the cable. Accordingly, the amount of moisture is measured on the basis of the reciprocating delay time and the propagation transmission time acquired from the reflection coefficient.

DESCRIPTION OF EMBODIMENTS

Hereinafter, modes for embodying the present technology (hereinafter referred to as embodiments) will be described below. The description will be made in the following order.
1. First embodiment (example of obtaining reciprocating delay time and propagation transmission time)
2. Second embodiment (example of obtaining reciprocating delay time and propagation transmission time using single semiconductor chip)
3. Third embodiment (example of obtaining reciprocating delay time and propagation transmission time by performing wireless communication)
4. Fourth embodiment (example of obtaining reciprocating delay time and propagation transmission time by changing transmission direction)

1. First Embodiment

[Configuration Example of Measurement Device]

Figure 1:
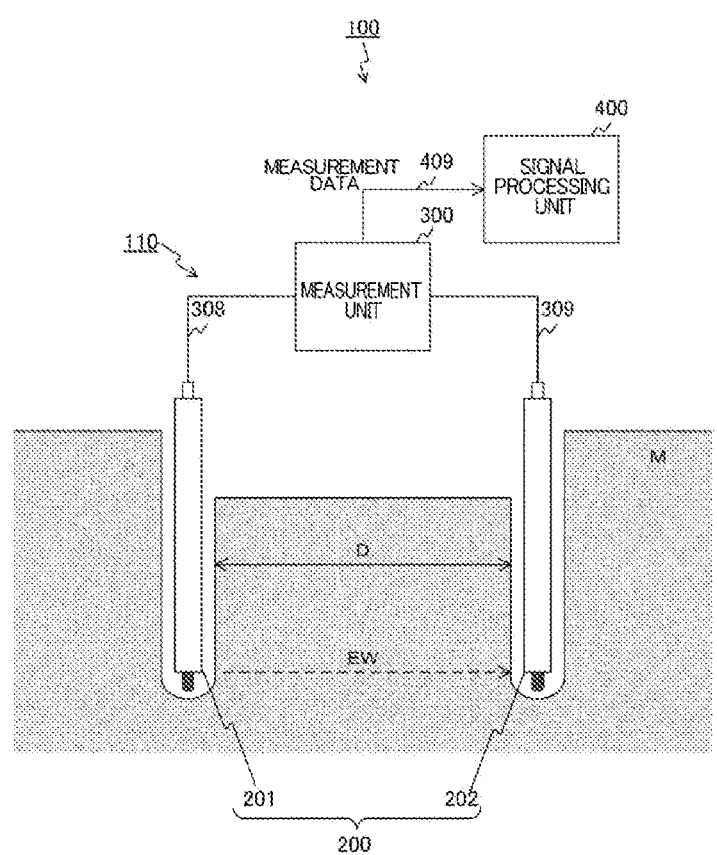
FIG. 1 is a block diagram illustrating a configuration example of a measurement device in a first embodiment of the present technology.

FIG. 1 is a diagram showing a configuration example of a measurement device 100 in a first embodiment of the present technology. The measurement device 100 measures an amount of moisture contained in a medium M and includes a sensor device 110 and a signal processing unit 400. As the medium M, for example, soil for growing crops may be conceived.

The sensor device 110 acquires data necessary to measure an amount of moisture as measurement data. Details of the measurement data will be described later. The sensor device 110 transmits the measurement data to the signal processing unit 400 through a signal line 409. The signal processing unit 400 measures the amount of moisture using the measurement data.

In addition, the sensor device 110 includes a sensor head 200 and a measurement unit 300. The sensor head 200 is a part composed of probes 201 and 202. These probes 201 and 202 are connected to the measurement unit 300 through cables 308 and 309. As the cables 308 and 309, for example, coaxial cables are used. These cables 308 and 309 are connected to the probes 201 and 202 in such a manner that the tips thereof are embedded into the inside of the probes 201 and 202. The measurement unit 300 causes one of the probes 201 and 202 to transmit electromagnetic waves EW and causes the other to receive the electromagnetic waves EW to generate measurement data.

In addition, the measurement unit 300 and the signal processing unit 400 are mounted in different semiconductor chips. Further, circuits of the measurement unit 300 and the signal processing unit 400 can be mounted in the same semiconductor chips, as described later.

Further, the measurement unit 300 may include an electronic circuit board including a wiring layer and a semiconductor chip mounted on the electronic circuit board. The measurement unit 300 may include the electronic circuit board, the semiconductor chip, and a housing accommodating the electronic circuit board and the semiconductor chip. In addition, the cables 308 and 309 may be connected to the semiconductor chip through the wiring layer included in the electronic circuit board.

The measurement unit 300 including the electronic circuit board and the semiconductor chip or the housing accommodating it may have (1) a size falling within an approximately rectangular shape in which a size in an extending direction (a direction of the plane of the electronic circuit board) is, for example, 1 to 20 centimeters (cm) in length of one side and 1 to 40 centimeters (cm) in length of the other side perpendicular to this one side, and (2) a thickness of, for example, 2 to 20 millimeters (mm).

A direction in which the measurement unit 300 is disposed may take any of at least two directions. That is, (1) the measurement unit 300 may be disposed such that a direction in which the measurement unit 300 extends is parallel to a direction in which the probes 201 and 202 extend. Otherwise, (2) the measurement unit 300 may be disposed such that the direction in which the measurement unit 300 extends is perpendicular to the direction in which the probes 201 and 202 extend.

Meanwhile, when the signal processing unit 400 is disposed in a housing different from that of the sensor device 110, a system including the sensor device 110 and the signal processing unit 400 can be handled as a measurement system.

[Configuration Example of Sensor Head]

Figure 2:
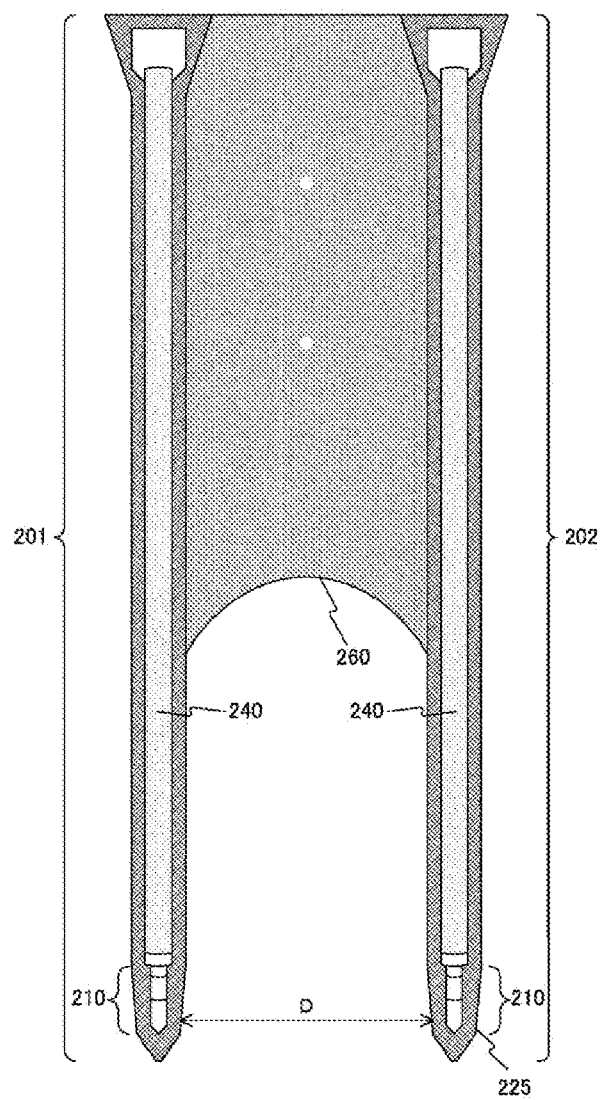
FIG. 2 is an example of an external view of a sensor head in the first embodiment of the present technology.

FIG. 2 is example of an external view of the sensor head 200 in the first embodiment of the present technology. The sensor head 200 includes the probes 201 and 202. The length of each of the probes 201 and 202 is, for example, 75 to 150 millimeters (mm). The thickness (diameter or the width of the probe cross section) of each of the probes 201 and 202 is, for example, 3 to 30 millimeters (mm). These probes 201 and 202 are disposed in a medium such as soil and respectively include antenna parts 210 capable of transmitting/receiving electromagnetic waves at a predetermined frequency between the probes 201 and 202.

The probes 201 and 202 are embedded in the medium such that a distance between the antenna parts 210 reaches a predetermined value D. For example, these probes are embedded in the medium in an almost vertical posture. Meanwhile, if the distance between the antenna parts 210 reaches D, the posture of the probes is not limited to a vertical posture.

The antenna parts 210 are provided at the tips (in other words, ends) of the probes 201 and 202 or in the vicinity thereof and transmit/receive electromagnetic waves. Meanwhile, although the antenna parts 210 may be provided at the tips of the probes 201 and 202, the present technology is not limited to this configuration. For example, the antenna parts 210 can also be provided at center positions of the probes 201 and 202, and the like.

Further, the antenna parts 210 are composed of microantennas formed in a size in which they do not cause the probes 201 and 202 to resonate. Accordingly, it is possible to curb deterioration of measurement accuracy due to resonance of the probes 201 and 202.

In addition, the tips of the cables 308 and 309 (coaxial cables) in FIG. 1 are embedded inside the probes 201 and 202, as described above. Parts of these coaxial cables are opened and used as the antenna parts 210. The outer circumferences of parts of the coaxial cables other than the antenna parts 210 are covered with an electromagnetic wave absorbing material 240. It is possible to curb leaking of electromagnetic waves from regions other than the opening parts using the electromagnetic wave absorbing material 240.

Although a Ni—Zn based ferrite is mainly used as the electromagnetic wave absorbing material 240, the present technology is not limited thereto and other materials having high dielectric constants such as sendust and permalloy may be used depending on the frequency of the electromagnetic waves EW. In addition, the electromagnetic wave absorbing material 240 may be omitted as necessary or may be provided on only one of the probes 201 and 202.

The size of the distance D between the antenna parts 210 is not particularly limited. When the distance D is excessively long, attenuation of the electromagnetic waves EW propagating through the medium M increases and thus a sufficient reception strength may not be obtained. On the other hand, when the distance D is excessively short, measurement may become technically difficult. In consideration of this, the distance D is set to an appropriate value. For example, the distance D may be 25 to 75 millimeters (mm).

In addition, a spacer 260 for defining the distance between the antenna parts 210 is disposed between the probes 201 and 202. Further, the outer circumference of each of the probes 201 and 202 is covered by an outer shell 225 having a thickness of 1 to 3 millimeters (mm) and isolated from the medium. The spacer 260 and the outer shell 225 are formed of an electromagnetic wave transmitting material. As the electromagnetic wave transmitting material, for example, inorganic materials such as polymer materials, glass, and polytetrafluoroethylene (PTEF) may be conceived. Polycarbonate (PC), polyethersulfone (PES), polyetheretherketone (PEEK), polystyrene sulfonic acid (PSS), and the like may be used as polymer materials. In addition, polymethylmethacrylate (PMMA), polyethylene terephthalate (PET), and the like may be used as polymer material.

The thickness of the spacer 260 may be less than the size and the thickness of the measurement unit 300 including the electronic circuit board and the semiconductor chip. For example, when the measurement unit 300 is disposed such that the direction in which the measurement unit 300 extends is parallel to the direction in which the probes 201 and 202 extend, the thickness of the spacer 260 may be less than the thickness of the measurement unit 300, desirably, is less than ½ thereof, and more desirably, is less than ⅓ thereof. Alternatively, when the measurement unit 300 is disposed such that the direction in which the measurement unit 300 extends is perpendicular to the direction in which the probes 201 and 202 extend, the thickness of the spacer 260 may be less than the length of the measurement unit 300 in the extending direction thereof, desirably, is less than ½ thereof, and more desirably, is less than ⅓ thereof. In addition, the thickness of the spacer 260 may be less than the thickness (diameter or the width of the probe cross section) of at least any one of the probes 201 and 202, desirably, is less than ½ thereof, and more desirably, is less than ⅓ thereof. Further, the thickness of the spacer 260 may be, for example, 1 to 3 millimeters (mm).

The configuration in which the thickness of the spacer 260 is less than the thickness of the measurement unit 300, less than the length of the measurement unit 300 in the extending direction thereof, or less than the thickness (diameter or the width of the probe cross section) of at least any one of the probes 201 and 202 is effective in a moisture sensor that measures a propagation delay time of electromagnetic waves between antennas. Even if the spacer 260 is formed of an electromagnetic wave transmitting material, there is a possibility that electromagnetic waves radiated from the transmission antenna may be reflected by the spacer and received by the reception antenna to become noise according to the material. By employing the aforementioned configuration with respect to the thickness of the spacer 260, the aforementioned noise reflected by the spacer 260 can be reduced as compared to a form that does not include this configuration. This effect of reducing the noise by decreasing the thickness of the spacer does not occur in a moisture sensor other than a moisture sensor that measures a propagation delay time of electromagnetic waves between antennas and occurs in the moisture sensor that measures a propagation delay time of electromagnetic waves between antennas.

Meanwhile, it is desirable that a distance d from the antenna parts (210 and 220) of the pair of probes 201 and 202 to the lower end of the spacer 260 be greater than the distance D between the antennas. Particularly, it is desirable that the distance d be greater than twice the distance D between the antennas. Further, it is more desirable that the distance d be greater than three times the distance D between the antennas and less than the length of the probes 201 and 202. Even if the spacer 260 between the probes 201 and 202 is formed of an electromagnetic wave transmitting material, there is a possibility that micro waves radiated from the transmission antenna may be reflected by the spacer and received by the reception antenna to become noise according to the material. As described above, the noise can be reduced by separating the spacer 260 from the antennas. This "effect of reducing the noise by separating the spacer 260 from the antennas" does not occur in a moisture sensor other than a moisture sensor using a method of measuring a propagation delay between antennas and occurs in a moisture sensor using the method of measuring a propagation delay between antennas as in the present technology.

In addition, an outer edge of the spacer 260 which is close to the antenna parts (210 and 220) between outer edges extending between the pair of probes (201 and 202) has an arc shape as illustrated in the figure. When the outer edge is arc-shaped instead of a straight line, noise derived from micro waves, radiated from the transmission antenna and reflected by the spacer 260, and received by the reception antenna can be further reduced. This "effect of reducing the noise by forming the spacer 260 in an arc shape" does not occur in a moisture sensor other than a moisture sensor using a method of measuring a propagation delay between antennas and occurs in a moisture sensor using the method of measuring a propagation delay between antennas.

[Configuration Example of Antenna Part]

Figure 3:
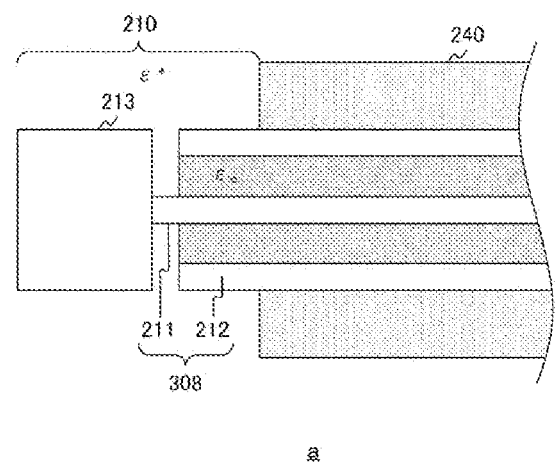
FIG. 3 is a diagram illustrating an example of an antenna part and an equivalent circuit in the first embodiment of the present technology.
Figure 3:
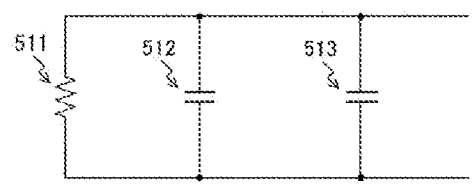

FIG. 3 is a diagram illustrating an example of the antenna part 210 and an equivalent circuit in the first embodiment of the present technology. In the figure, a is an enlarged view of the antenna part 210. In the figure, b is an example of an equivalent circuit of the antenna part 210.

The cable 308 (coaxial cable or the like) embedded in the probe 201 includes a core wire part 211 and a shield part 212. The thickness and the length of the cable are not particularly limited and can be set to an arbitrary thickness and length. As illustrated in a in the figure, the core wire part 211 is formed of a copper wire and the shield part 212 is formed of a copper pipe, but the shield part 212 may be formed of a copper wire mesh.

Apart near the tip of the cable 308 (coaxial cable or the like) is opened and an electrode part 213 is attached thereto. Accordingly, the antenna part 210 of each of the probes 201 and 202 serves as a micro-dipole antenna having a length of about 4 to 10 millimeters (mm). The opening part has an opening shape such as a square, a circle, an oval, or an ellipse. Along axis of the opening part may be appropriately set in response to the wavelength of electromagnetic waves to be used.

In addition, as illustrated in b in the figure, the equivalent circuit of the antenna part 210 is represented as a circuit in which a resistor 511 and fringing capacitors 512 and 513 are connected in parallel. The capacitance of the fringing capacitor 512 is a value in response to a dielectric $\varepsilon_c$ of a material extending inside the coaxial cable. The capacitance of the fringing capacitor 513 is a value in response to a dielectric $\varepsilon^*$ of a material extending around the electrode 513.

When an electrical signal is transmitted to any of the probes 201 and 202, a part of the signal is reflected at the ends and thus the electrical signal reciprocates in the coaxial cable. In this electrical signal, a wave in the input signal is assumed to be an "incident wave" and a wave obtained from reflection of the incident wave is assumed to be a "reflected wave."

Here, a comparative example in which the outer shell 225 is not provided is conceived. In this comparative example, a reciprocating delay time necessary for an electrical signal to reciprocate in the coaxial cable varies caused by temperature and the dielectric constant $\varepsilon^*$ of a medium.

Since the coaxial cable lengthens according to thermal expansion as the temperature increases, the delay time increases. In addition, when the dielectric constant $\varepsilon^*$ of the medium changes, the fringing capacitor 512 changes in response to the value and a peak time of an impulse response of a reflection coefficient changes. Here, the reflection coefficient is a ratio between complex amplitudes of an incident wave and a reflected wave.

Figure 4:
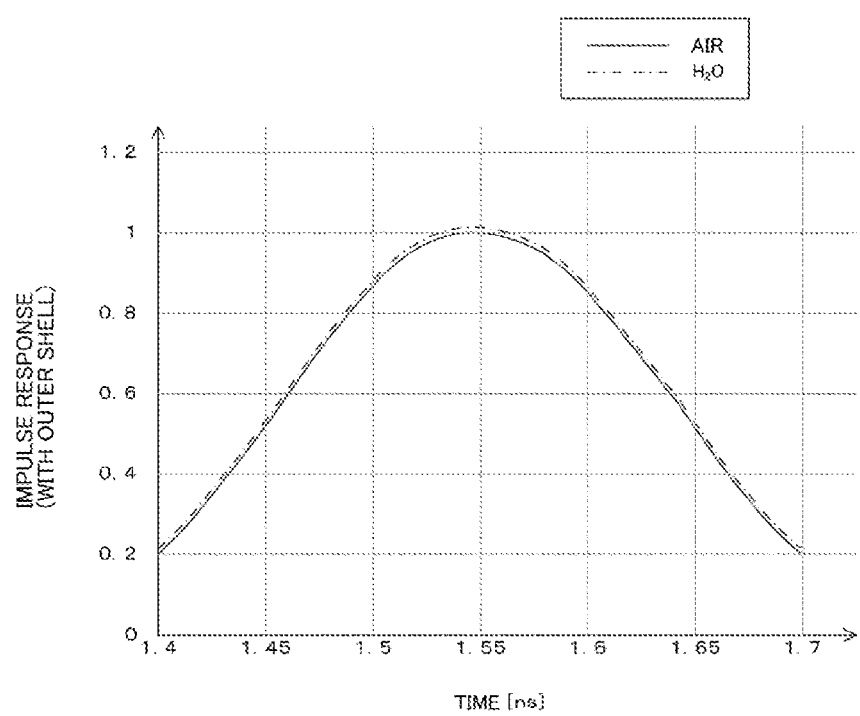
FIG. 4 is a graph showing an example of impulse response waveforms of a reflection coefficient in the first embodiment of the present technology.

FIG. 4 is a graph showing an example of impulse response waveforms of a reflection coefficient in the first embodiment of the present technology. In the figure, a vertical axis represents an impulse response of the reflection coefficient and a horizontal axis represents time. A solid-line curve represents an impulse response waveform when a medium is the air, and an alternate-long-and-short-dash-line curve represents an impulse response waveform when a medium is water.

Figure 5:
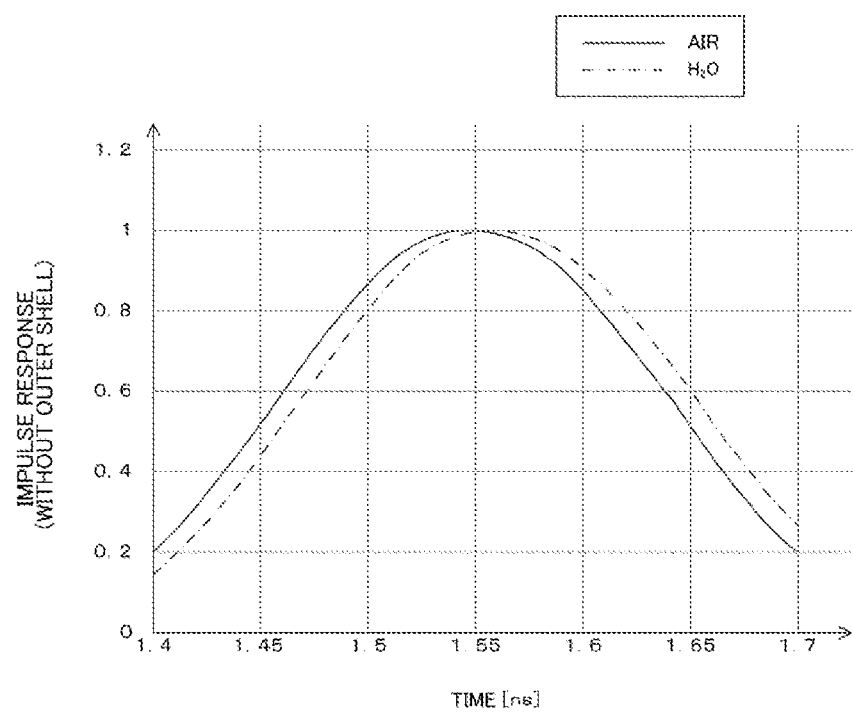
FIG. 5 is a graph showing an example of impulse response waveforms of a reflection coefficient in a comparative example.

FIG. 5 is a graph showing an example of impulse response waveforms of a reflection coefficient in a comparative example in which the outer shell 225 is not provided. In the figure, a vertical axis represents an impulse response of the reflection coefficient and a horizontal axis represents time. A solid-line curve represents an impulse response waveform when a medium is the air, and an alternate-long-and-short-dash-line curve represents an impulse response waveform when a medium is water.

As illustrated in FIG. 5, in a case where the outer shell 225 is not provided, when the medium changes, the dielectric constant $\varepsilon^*$ varies and the fringing capacitor 512 changes. Accordingly, a peak value of the impulse response varies. An error is generated in calculation of a reciprocating delay time caused by this variation.

On the other hand, when the outer shell 225 is provided to isolate the antenna part 210 from the medium, the fringing capacitor 512 becomes constant, and thus the peak value of the impulse response does not vary as illustrated in FIG. 4. Accordingly, the reciprocating delay time can be calculated with high accuracy.

Figure 6:
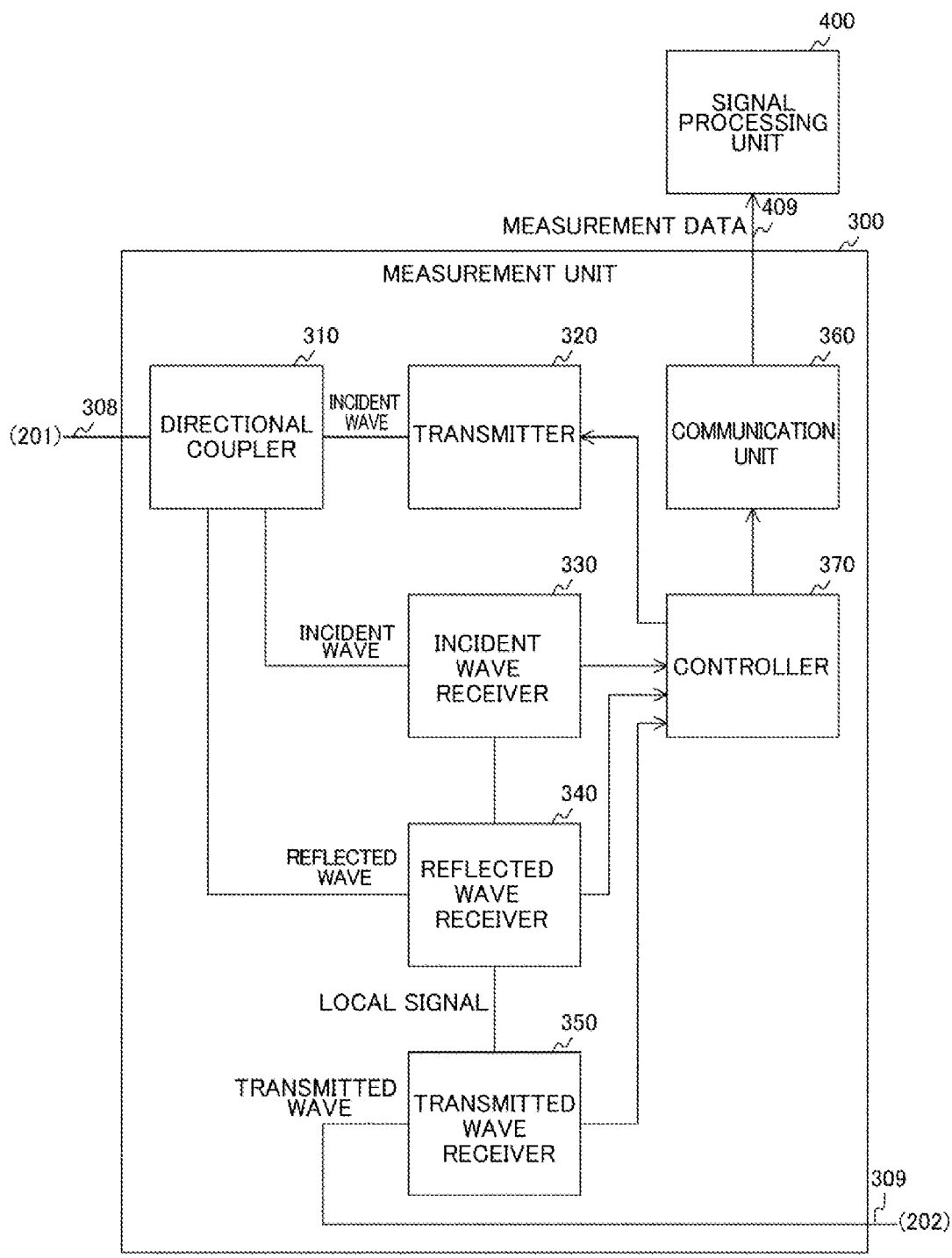
FIG. 6 is a block diagram illustrating a configuration example of a measurement unit in the first embodiment of the present technology.

FIG. 6 is a block diagram illustrating a configuration example of the measurement unit 300 in the first embodiment of the present technology. The measurement unit 300 includes a directional coupler 310, a transmitter 320, an incident wave receiver 330, a reflected wave receiver 340, a transmitted wave receiver 350, a communication unit 360, and a controller 370. For example, a vector network analyzer may be used as the measurement unit 300.

The directional coupler 310 separates an electrical signal transmitted through the cable 308 into an incident wave and a reflected wave. The incident wave is a wave of an electrical signal transmitted from the transmitter 320 and the reflected wave is obtained from reflection of the incident wave at the end of the probe 201. The directional coupler 310 provides the incident wave to the incident wave receiver 330 and provides the reflected wave to the reflected wave receiver 340.

The transmitter 320 transmits an electrical signal at a predetermined frequency to the probe 201 through the directional coupler 310 and the cable 308 as a transmission signal. As an incident wave in the transmission signal, for example, a continuous wave (CW) may be used. The transmitter 320 transmits the transmission signal by sequentially switching the frequency in a step of 50 megahertz (MHz), for example, in a frequency band of 1 to 9 gigahertz (GHz).

The incident wave receiver 330 receives the incident wave from the directional coupler 310. The reflected wave receiver 340 receives the reflected wave from the directional coupler 310. The transmitted wave receiver 350 receives a transmitted wave from the probe 202. Here, the transmitted wave is obtained by converting an electromagnetic wave transmitted through the medium between the probes 201 and 202 into an electrical signal by the probe 202.

The incident wave receiver 330, the reflected wave receiver 340, and the transmitted wave receiver 350 perform quadrature detection and analog-to-digital (AD) conversion on the received incident wave, reflected wave, and transmitted wave and provide the resultant waves to the controller 370 as reception data.

Meanwhile, the incident wave receiver 330, the reflected wave receiver 340, and the transmitted wave receiver 350 are an example of a receiver in the claims.

The controller 370 performs control of the transmitter 320 to cause the transmission signal including the incident wave to be transmitted and processing of obtaining a reflection coefficient and a transmission efficient. Here, the reflection coefficient is a ratio between complex amplitudes of the incident wave and the reflected wave, as described above.

The transmission coefficient is a ratio between complex amplitudes of the incident wave and the transmitted wave. The controller 370 provides the obtained reflected coefficient and transmission coefficient to the communication unit 360.

The communication unit 360 transmits data representing the reflection coefficient and the transmission coefficient to the signal processing unit 400 through a signal line 409 as measurement data.

Meanwhile, to measure an accurate reflection coefficient and transmission coefficient, calibration of frequency characteristics of the directional coupler 310, the transmitter 320, and the receiver (incident wave receiver 330 and the like) is executed before measurement.

[Configuration Example of Directional Coupler]

Figure 7:
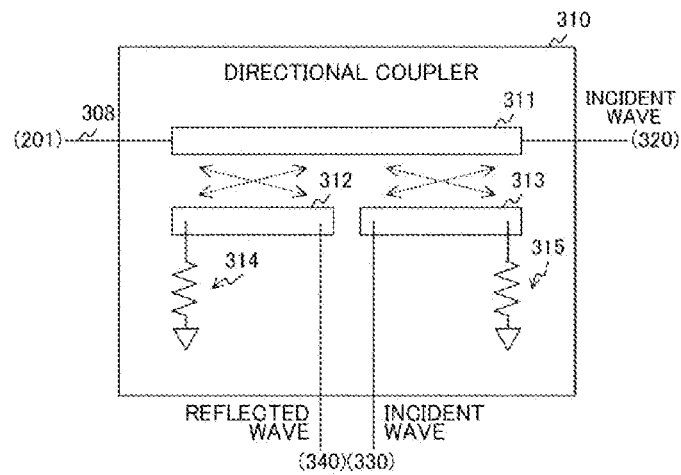
FIG. 7 is a diagram illustrating a configuration example of a directional coupler in the first embodiment of the present technology.

FIG. 7 is a diagram showing a configuration example of the directional coupler 310 in the first embodiment of the present technology. The directional coupler 310 includes transmission lines 311, 312, and 313 and terminating resistors 314 and 315. The directional coupler 310 can be implemented as, for example, a bridge coupler suitable for miniaturization.

One end of the transmission line 311 is connected to the transmitter 320 and the other end is connected to the probe 201 through the cable 308. The transmission line 312 is shorter than the transmission line 311 and is a line coupled to the transmission line 311 through electromagnetic field coupling. One end of the transmission line 312 is connected to the terminating resistor 314 and the other end is connected to the reflected wave receiver 340. The transmission line 313 is shorter than the transmission line 311 and is a line coupled to the transmission line 311 through electromagnetic field coupling. One end of the transmission line 313 is connected to the terminating resistor 315 and the other end is connected to the incident wave receiver 330.

According to the above-described configuration, the directional coupler 310 separates an electrical signal into an incident wave and a reflected wave and provides the incident wave and the reflected wave to the incident wave receiver 330 and the reflected wave receiver 340.

[Configuration Example of Transmitter and Receiver]

Figure 8:
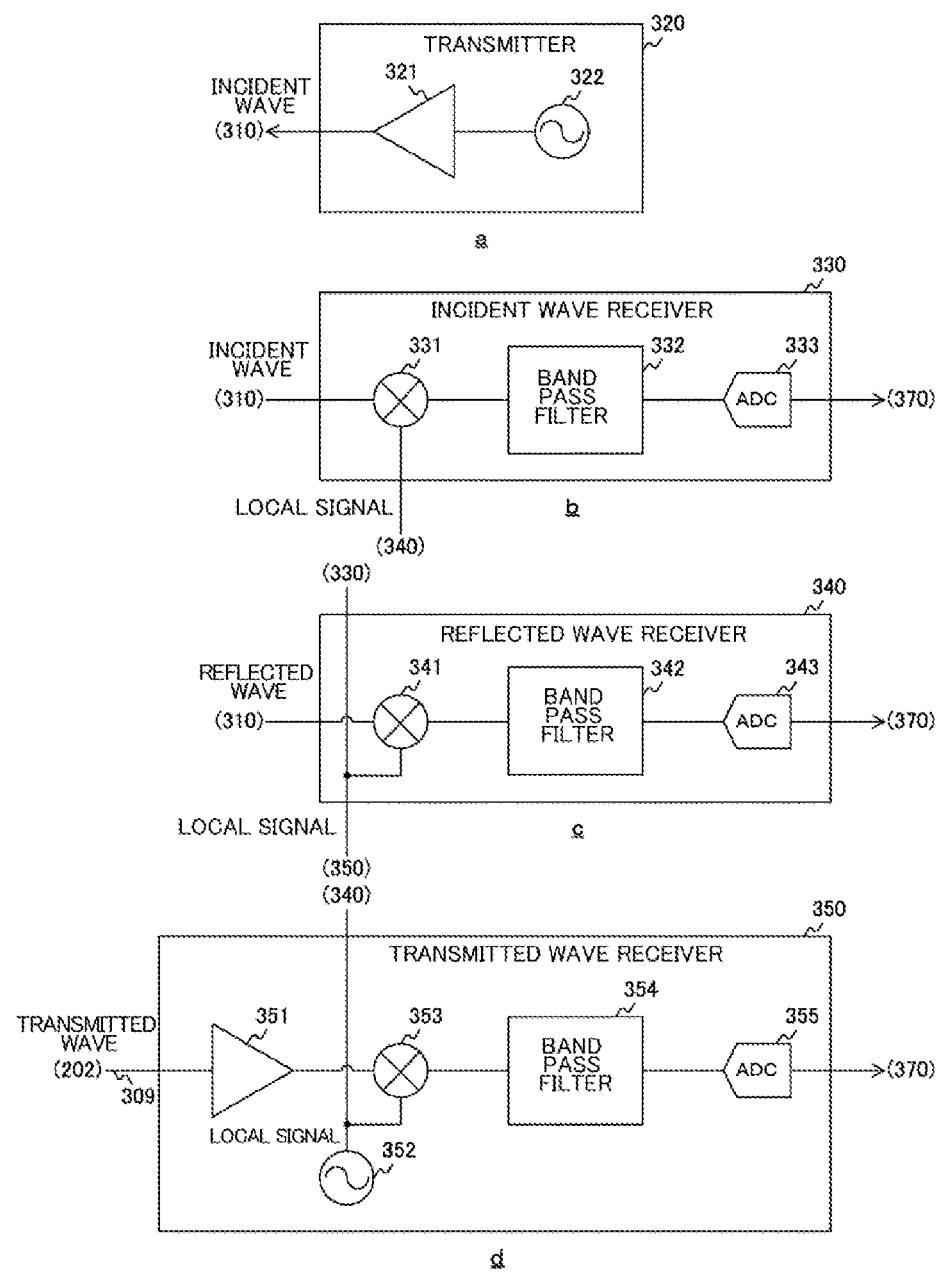
FIG. 8 is a circuit diagram illustrating a configuration example of a transmitter and a receiver in the first embodiment of the present technology.

FIG. 8 is a circuit diagram illustrating a configuration example of the transmitter 320 and the receivers in the first embodiment of the present technology. In the figure, a is a circuit diagram illustrating a configuration example of the transmitter 320 and b is a circuit diagram illustrating a configuration example of the incident wave receiver 330. In the figure, c is a circuit diagram illustrating a configuration example of the reflected wave receiver 340 and d is a circuit diagram illustrating a configuration example of the transmitted wave receiver 350.

As illustrated in a in the figure, the transmitter 320 includes a transmission signal oscillator 322 and a driver 321.

The transmission signal oscillator 322 generates an electrical signal as a transmission signal according to control of the controller 370. The driver 321 outputs the transmission signal to the directional coupler 310. The transmission signal S(t) is represented by the following formula, for example.

$S(t)=|A|\cos(2\pi ft+\theta)$

In the above formula, t represents time and the unit is, for example, nanosecond (ns). |A| represents the amplitude of the transmission signal. Cos( ) represents a cosine function. f represents a frequency and the unit is, for example, hertz (Hz). θ represents a phase and the unit is, for example, radian (rad).

As illustrated in b in the figure, the incident wave receiver 330 includes a mixer 331, a band pass filter 332, an analog-to-digital converter 333.

The mixer 331 performs quadrature detection by mixing two local signals having a phase difference of 90 degrees therebetween and the transmission signal. A complex amplitude composed of an in-phase component $I_I$ and a quadrature component $Q_I$ is obtained according to the quadrature detection. These in-phase component $I_I$ and quadrature component $Q_I$ are represented by the following formula, for example. The mixer 331 provides the complex amplitude to the analog-to-digital converter 333 through the band pass filter 332.

$I_I=|A|\cos(\theta)$ $Q_I=|A|\sin(\theta)$

In the above formula, sin( ) represents a sine function.

The band pass filter 332 passes a component of a predetermined frequency band. The analog-to-digital converter 333 performs AD conversion. The analog-to-digital converter 333 generates data representing the complex amplitude according to AD conversion and provides the data to the controller 370 as reception data.

As illustrated in c in the figure, the reflected wave receiver 340 includes a mixer 341, a band pass filter 342, and an analog-to-digital converter 343. The configurations of the mixer 341, the band pass filter 342, and the analog-to-digital converter 343 are the same as those of the mixer 331, the band pass filter 332, and the analog-to-digital converter 333. The reflected wave receiver 340 performs quadrature detection on a reflected wave to acquire a complex amplitude composed of an in-phase component $I_R$ and a quadrature component $Q_R$ and provides reception data representing the complex amplitude to the controller 370.

As illustrated in d in the figure, the transmitted wave receiver 350 includes a receiver 351, a local signal oscillator 352, a mixer 353, a band pass filter 354, and an analog-to-digital converter 355. The configurations of the mixer 353, the band pass filter 354, and the analog-to-digital converter 355 are the same as those of the mixer 331, the band pass filter 332, and the analog-to-digital converter 333.

The receiver 351 receives an electrical signal including a transmitted wave through the cable 309 and outputs the transmitted wave to the mixer 353. The local signal oscillator 352 generates two local signals having a phase difference of 90 degrees therebetween.

The transmitted wave receiver 350 performs quadrature detection on the transmitted wave to acquire a complex amplitude composed of an in-phase component $I_T$ and a quadrature component $Q_T$ and provides data representing the complex amplitude to the controller 370 as reception data.

Meanwhile, the circuits of the transmitter 320 and the receivers (incident wave receiver 330 and the like) are not limited to the circuits illustrated in the figure as long as they can transmit and receive an incident wave and the like.

[Configuration Example of Controller]

Figure 9:
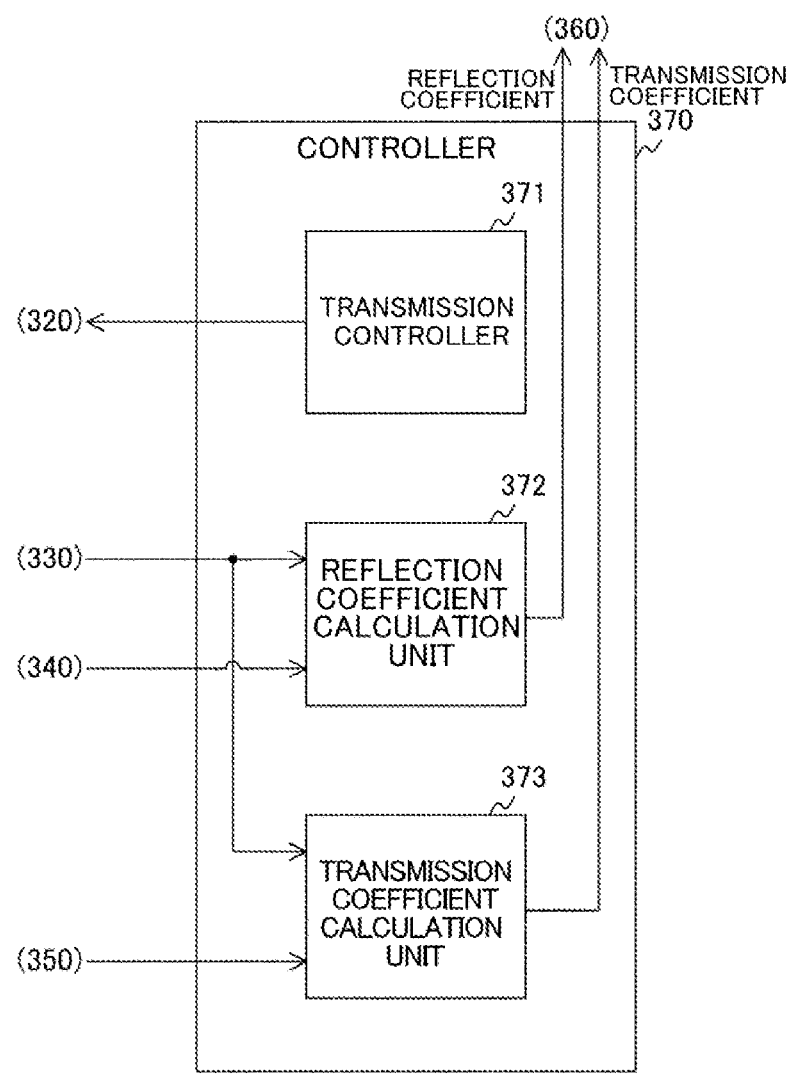
FIG. 9 is a block diagram illustrating a configuration example of a controller in the first embodiment of the present technology.

FIG. 9 is a block diagram illustrating a configuration example of the controller 370 in the first embodiment of the present technology. The controller 370 includes a transmission controller 371, a reflection coefficient calculation unit 372, and a transmission coefficient calculation unit 373.

The transmission controller 371 controls the transmitter 320 such that the transmitter 320 transmits a transmission signal.

The reflection coefficient calculation unit 372 calculates a reflection coefficient F for each frequency. The reflection coefficient calculation unit 372 receives complex amplitudes of an incident wave and a reflected wave from the incident wave receiver 330 and the reflected wave receiver 340 and calculates a ratio between the complex amplitudes as a reflection coefficient Γ according to the following formula.

$$\Gamma=(I_R+jQ_R)/(I_I+jQ_I)$$ Formula 1

In the above formula, j is an imaginary unit.

The reflection coefficient calculation unit 372 calculates reflection coefficients with respect to N (N is an integer) frequencies $f_1$ to $f_N$ according to Formula 1. These N reflection coefficients are denoted by $\Gamma_1$ to $\Gamma_N$. The reflection coefficient calculation unit 372 provides the reflection coefficients to the communication unit 360.

The transmission coefficient calculation unit 373 calculates a transmission coefficient T for each frequency. The transmission coefficient calculation unit 373 receives complex amplitudes of an incident wave and a transmitted wave from the incident wave receiver 330 and the transmitted wave receiver 350 and calculates a ratio between the complex amplitudes as a transmission coefficient T according to the following formula.

$$T=(I_T+jQ_T)/(I_I+jQ_I)$$ Formula 2

The transmission coefficient calculation unit 373 calculates transmission coefficients with respect to the N frequencies $f_1$ to $f_N$ according to Formula 2. These N reflection coefficients are denoted by $T_1$ to $T_N$. The transmission coefficient calculation unit 373 provides the transmission coefficients to the signal processing unit 400 through the communication unit 360.

[Configuration Example of Signal Processing Unit]

Figure 10:
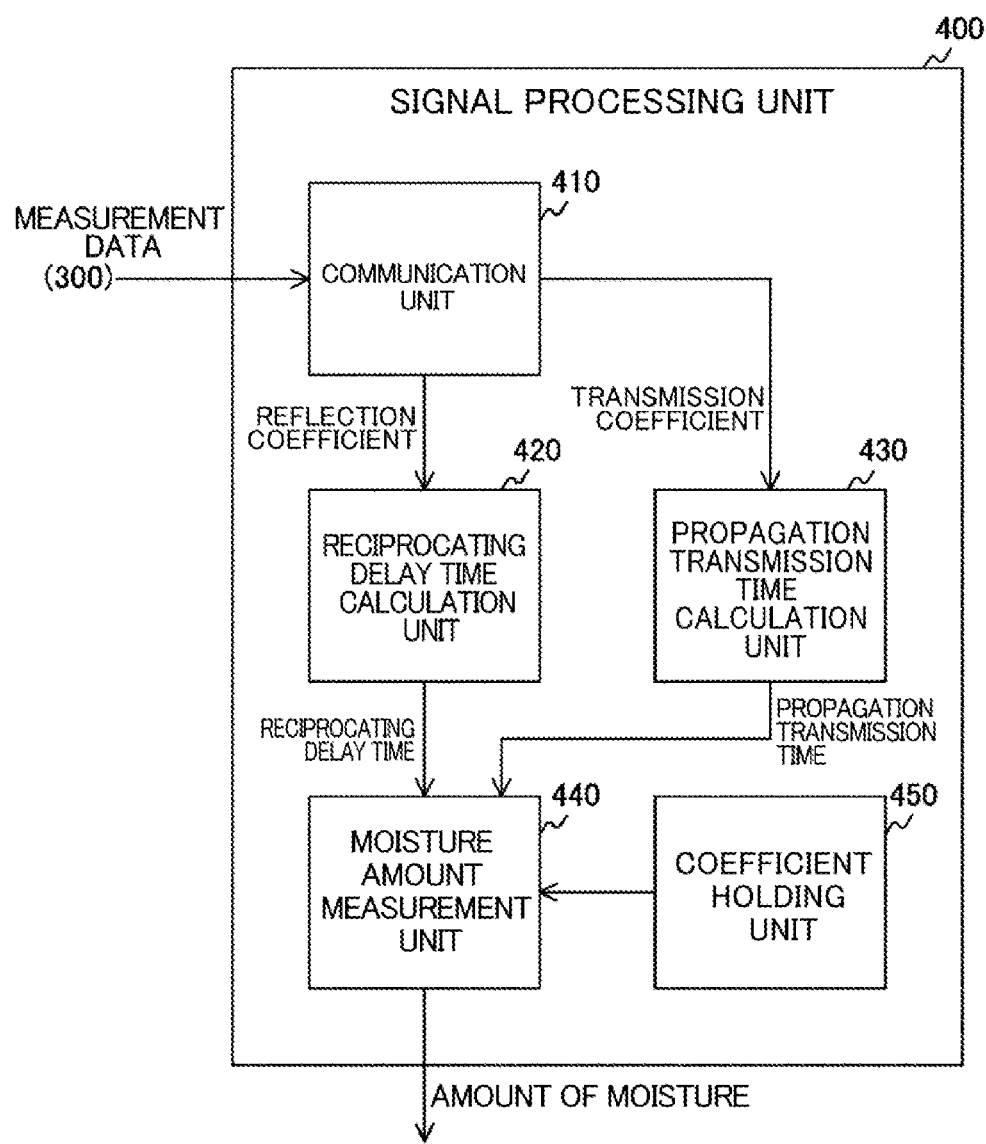
FIG. 10 is a block diagram illustrating a configuration example of a signal processing unit in the first embodiment of the present technology.

FIG. 10 is a block diagram illustrating a configuration example of the signal processing unit 400 in the first embodiment of the present technology. The signal processing unit 400 includes a communication unit 410, a reciprocating delay time calculation unit 420, a propagation transmission time calculation unit 430, a moisture amount measurement unit 440, and a coefficient storing unit 450.

The communication unit 410 receives measurement data from the measurement unit 300. The communication unit 410 provides reflection coefficients $\Gamma_1$ to $\Gamma_N$ in the measurement data to the reciprocating delay time calculation unit 420 and provides transmission coefficients $T_1$ to $T_N$ in the measurement data to the propagation transmission time calculation unit 430.

The reciprocating delay time calculation unit 420 calculates a time over which an electrical signal reciprocates in the cable 308 as a reciprocating delay time on the basis of the reflection coefficients. The reciprocating delay time calculation unit 420 obtains an impulse response $h_\Gamma(t)$ by performing inverse Fourier transform on the reflection coefficients $\Gamma_1$ to $\Gamma_N$. Then, the reciprocating delay time calculation unit 420 obtains a time difference between the timing of a peak value of the impulse response $h_\Gamma(t)$ and a CW transmission timing as a reciprocating delay time $\tau_{11}$ and provides it to the moisture amount measurement unit 440.

The propagation transmission time calculation unit 430 calculates a time over which electromagnetic waves propagate and an electrical signal is transmitted through the medium and the cables 308 and 309 as a propagation transmission time on the basis of the transmission coefficients. The propagation transmission time calculation unit 430 obtains an impulse response $h_T(t)$ by performing inverse Fourier transform on the transmission coefficients $T_1$ to $T_N$. Then, the propagation transmission time calculation unit 430 obtains a time difference between the timing of a peak value of the impulse response $h_T(t)$ and a CW transmission timing as a propagation transmission time $\tau_{21}$ and provides it to the moisture amount measurement unit 440.

The moisture amount measurement unit 440 measures the amount of moisture on the basis of the reciprocating delay time $\tau_{11}$ and propagation transmission time $\tau_{21}$. First, the moisture amount measurement unit 440 calculates a propagation delay time $\tau_d$ from the reciprocating delay time $\tau_{11}$ and propagation transmission time $\tau_{21}$. Here, the propagation delay time is a time over which electromagnetic waves propagate through the medium between the probes 201 and 202. The propagation delay time $\tau_d$ is calculated by the following formula.

$$\tau_d=\tau_{21}-\tau_{11}$$ Formula 3

In the above formula, the unit of the reciprocating delay time $\tau_{11}$, propagation transmission time $\tau_{21}$, and the propagation delay time $\tau_d$ is nanosecond (ns), for example.

Then, the moisture amount measurement unit 440 reads coefficients a and b representing a relationship between the amount of moisture and the propagation delay time $\tau_d$ from the coefficient storing unit 450 and measures the amount of moisture x by putting the propagation delay time $\tau_d$ calculated using Formula 3 into the following formula. In addition, the moisture amount measurement unit 440 outputs the measured amount of moisture to an external device or apparatus as necessary.

$$\tau_d=a\cdot x+b$$ Formula 4

In the above formula, the unit of the amount of moisture x is, for example, percent by volume (%).

The coefficient storing unit 450 stores the coefficients a and b. A nonvolatile memory is used as the coefficient storing unit 450.

Figure 11:
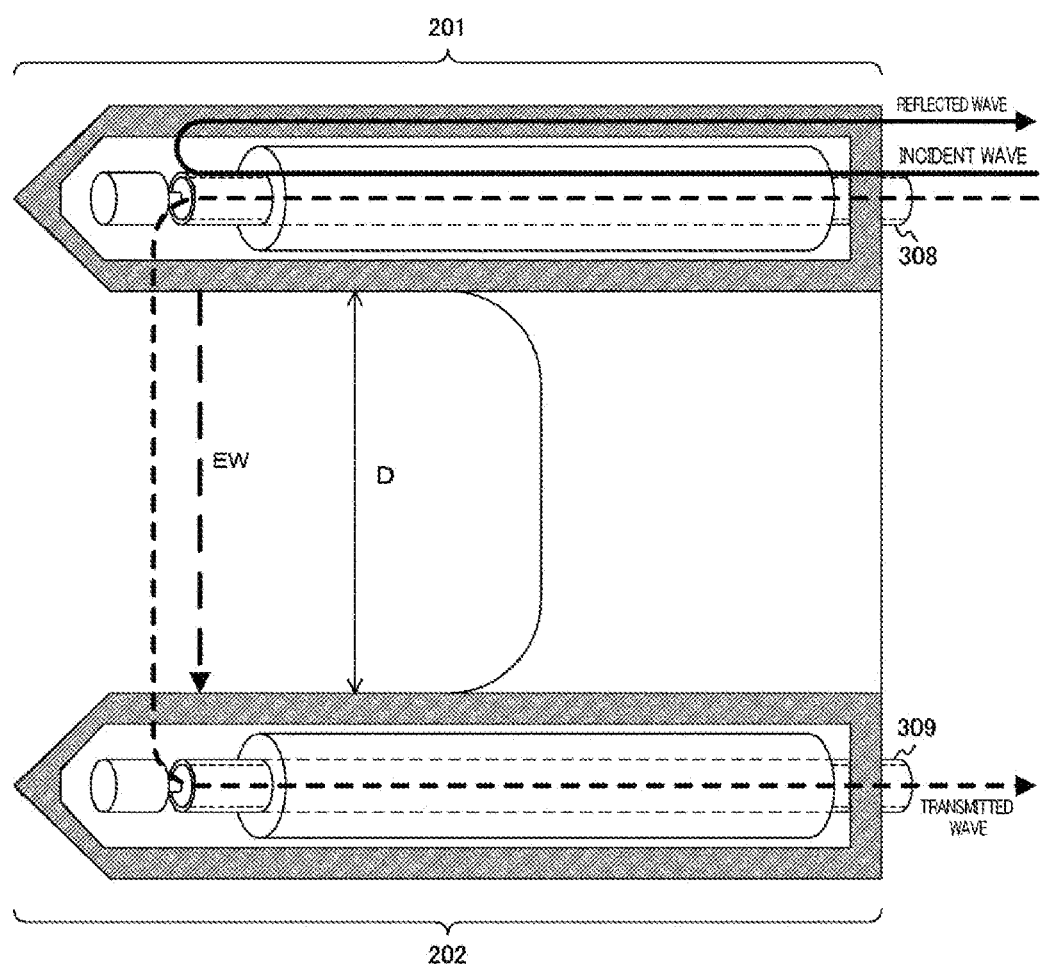
FIG. 11 is a diagram for describing a propagation path and a transmission path of electromagnetic waves and an electrical signal in the first embodiment of the present technology.

FIG. 11 is a diagram for describing a propagation path and a transmission path of electromagnetic waves and an electrical signal in the first embodiment of the present technology.

As described above, the transmitter 320 transmits an electrical signal including an incident wave to the probe 201 as a transmission signal through the cable 308 having the tip embedded in the probe 201.

The incident wave is reflected at the end of the probe 201 and the reflected wave is received by the reflected wave receiver 340. Accordingly, the electrical signal including the incident wave and the reflected wave reciprocates in the cable 308. In the figure, an arrow in a thick solid line indicates a path through which the electrical signal reciprocates in the cable 308. A time over which the electrical signal reciprocates through this path corresponds to the reciprocating delay time $\tau_{11}$.

In addition, the electrical signal including the incident wave is converted into electromagnetic waves EW by the probe 201 and the electromagnetic waves EW transmit (in other words, propagate) through the medium between the probes 201 and 202. The probe 202 converts the electromagnetic waves EW into an electrical signal. The transmitted wave receiver 350 receives a transmitted wave in the electrical signal through the cable 309. That is, the electrical signal including the incident wave is transmitted through the cable 308 and converted into the electromagnetic waves EW, the electromagnetic waves EW propagate through the medium and are converted into the electrical signal including the transmitted wave, and the electrical signal is transmitted through the cable 309. In the figure, an arrow in a thick dotted line indicates a path through which the electronic waves propagate and the electrical signal (incident wave and transmitted wave) is transmitted through the medium and the cables 308 and 309. A time over which the electromagnetic waves propagate and the electrical signal is transmitted through this path corresponds to the propagation transmission time $\tau_{21}$.

The controller 370 in the measurement unit 300 obtains the reflection coefficient Γ and the transmission coefficient T according to Formula 1 and Formula 2. Then, the signal processing unit 400 obtains the reciprocating delay time $\tau_{11}$ and the propagation transmission time $\tau_{21}$ from the reflection coefficient Γ and the transmission coefficient T.

Here, a path from transmission of the incident wave to reception of the transmitted wave includes the medium and the cables 308 and 309. Accordingly, the propagation delay time $\tau_d$ over which the electromagnetic waves propagates through the medium is obtained by a difference between the propagation transmission time 121 and a delay time over which the electrical signal is transmitted through the cables 308 and 309. Here, if the cables 308 and 309 are assumed to have the same length, a delay time over which the electrical signal is transmitted through the cable 308 and a delay time over which the electrical signal is transmitted through the cable 309 are identical. In this case, the sum of the delay times over which the electrical signal is transmitted through the cables 308 and 309 becomes identical to the reciprocating delay time $\tau_{11}$ over which the electrical signal reciprocates through the cable 308. Accordingly, Formula 3 is established and the signal processing unit 400 can calculate the propagation delay time $\tau_d$ according to Formula 3.

Then, the signal processing unit 400 calculates a propagation transmission time from the obtained reciprocating delay time $\tau_{11}$ and propagation transmission time 121 and performs processing of measuring the amount of moisture contained in the medium from the propagation transmission time and the coefficients a and b. Meanwhile, the signal processing unit 400 is an example of a processing unit in the claims.

Figure 12:
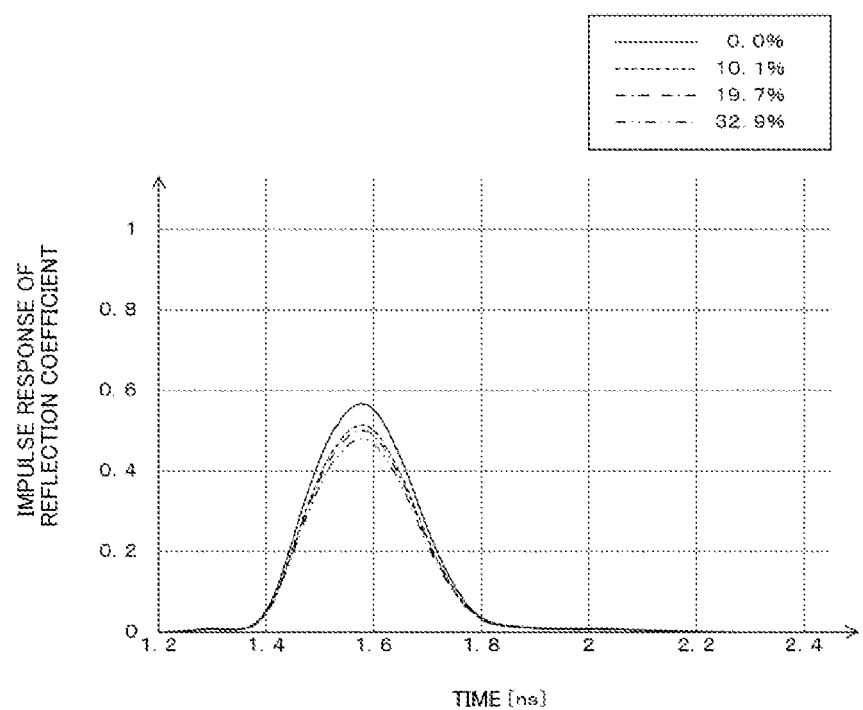
FIG. 12 is a graph showing an example of impulse response waveforms of a reflection coefficient in the first embodiment of the present technology.

FIG. 12 is a graph showing an example of impulse response waveforms of a reflection coefficient in the first embodiment of the present technology. In the figure, a vertical axis represents an impulse response of the reflection coefficient and a horizontal axis represents time.

It is assumed that four types of Toyoura standard sand having different amounts of moisture are prepared as media and the measurement device 100 obtains impulse responses of reflection coefficients. It is assumed that the amounts of moisture are 0.0, 10.1, 19.7, and 32.9 percent by volume (%).

As illustrated in the figure, a peak value of the reflection coefficient does not change even if the amount of moisture changes. That is, the reciprocating delay time is constant. This is because the probes 201 and 202 are isolated by the outer shell 225, as described above.

Figure 13:
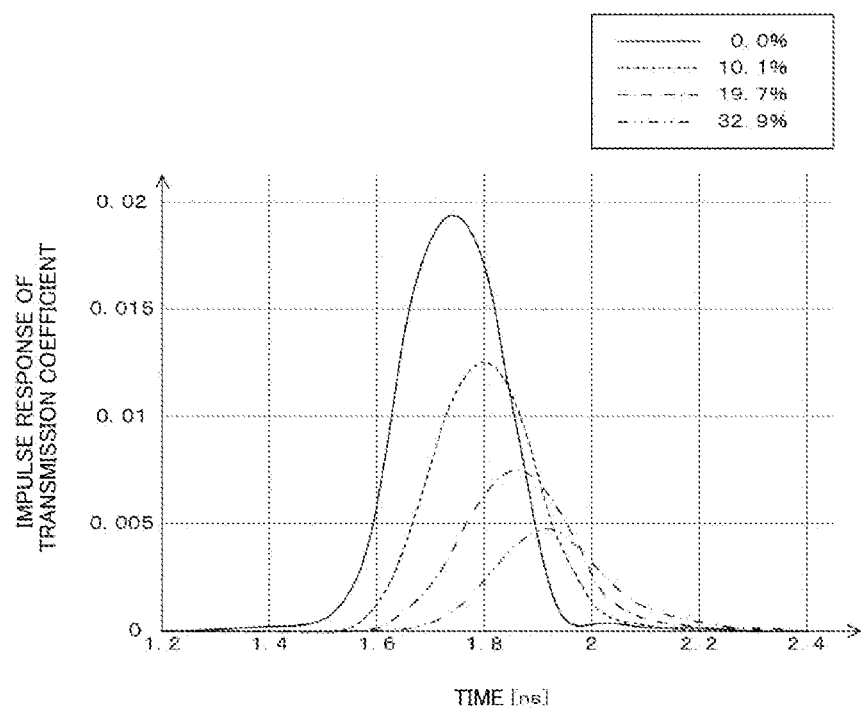
FIG. 13 is a graph showing an example of impulse response waveforms of a transmission coefficient in the first embodiment of the present technology.

FIG. 13 is a graph showing an example of impulse response waveforms of a transmission coefficient in the first embodiment of the present technology. In the figure, a vertical axis is an impulse response of the transmission coefficient and a horizontal axis is time. In the figure, media that are measurement targets are four types of Toyoura standard sand as in FIG. 12.

As illustrated in the figure, the timing of a peak value of the transmission coefficient is delayed as the amount of moisture increases. Accordingly, the propagation transmission delay time increases as the amount of moisture increases.

Figure 14:
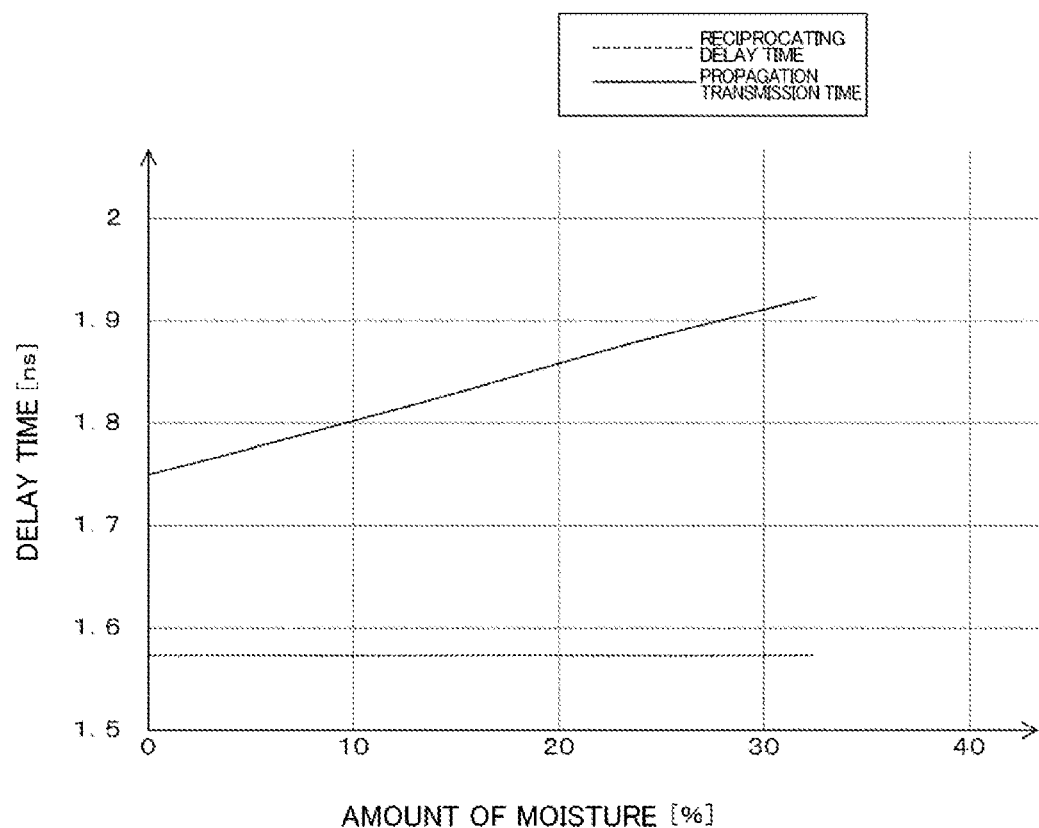
FIG. 14 is a graph showing an example of a relationship between a reciprocating delay time and a propagation transmission time and an amount of moisture in the first embodiment of the present technology.

FIG. 14 is a graph showing an example of a relationship between a reciprocating delay time and a propagation transmission time and an amount of moisture in the first embodiment of the present technology. In the figure, a vertical axis represents a reciprocating delay time or a propagation transmission time and a horizontal axis represents an amount of moisture.

In FIG. 14, a dotted line indicates a relationship between the reciprocating delay time and the amount of moisture obtained from FIG. 12. In FIG. 14, a solid line indicates a relationship between the propagation transmission time and the amount of moisture obtained from FIG. 13. As illustrated in FIG. 14, the reciprocating delay time is constant irrespective of the amount of moisture. On the other hand, the propagation transmission delay time increases as the amount of moisture increases.

Figure 15:
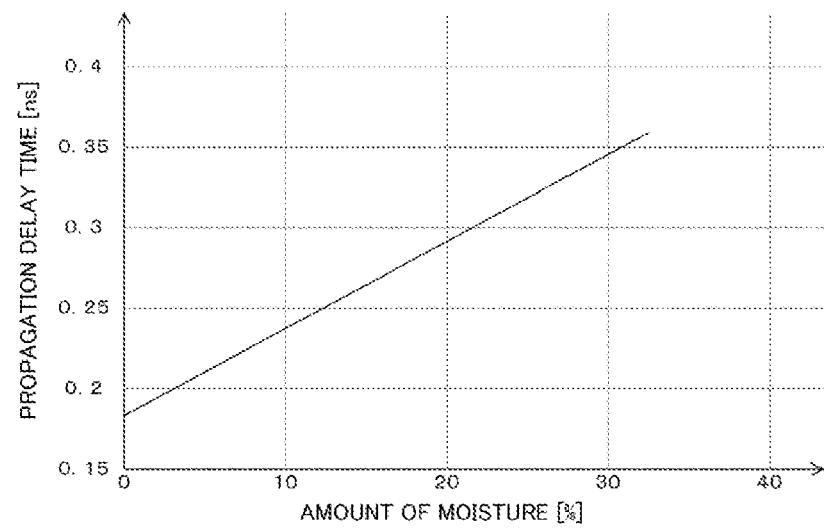
FIG. 15 is a graph showing an example of a relationship between a propagation delay time and an amount of moisture in the first embodiment of the present technology.

FIG. 15 is a graph showing an example of a relationship between a propagation delay time and an amount of moisture in the first embodiment of the present technology. In the figure, a vertical axis represents a propagation delay time and a horizontal axis represents an amount of moisture. In the figure, a straight line is acquired by obtaining a difference between the propagation transmission time and the reciprocating delay time for each amount of moisture in FIG. 14.

As illustrated in FIG. 15, the propagation delay time increases as the amount of moisture increases, and thus both are in a proportional relationship. Accordingly, Formula 4 is established. The coefficient a in Formula 4 is a slope of the straight line in the figure and the coefficient b is the intercept.

Figure 16:
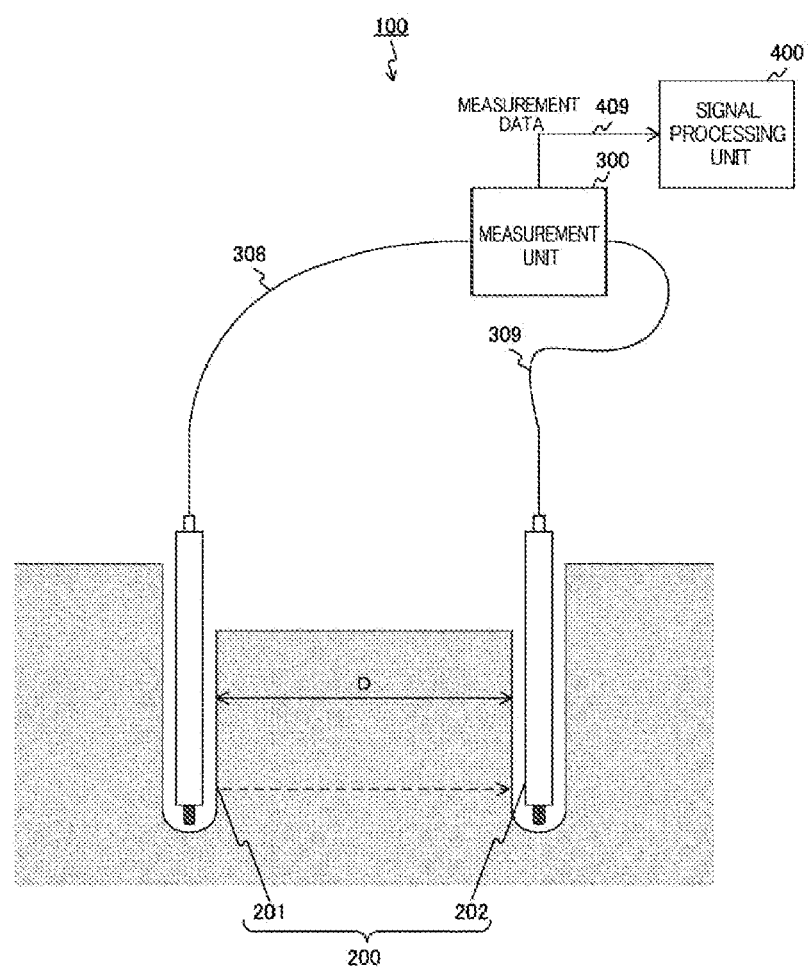
FIG. 16 is a block diagram illustrating a configuration example of a measurement device having an additionally extended cable in the first embodiment of the present technology.

FIG. 16 is a block diagram illustrating a configuration example of a measurement device having the additionally extended cables 308 and 309 in the first embodiment of the present technology. By lengthening the cables 308 and 309, the measurement unit 300 and the signal processing unit 400 can be disposed far away from the probes 201 and 202.

However, variation in the reciprocating delay time accompanied by temperature change increases as the cables 308 and 309 lengthen. Accordingly, if the measurement device 100 measures the amount of moisture having the reciprocating delay time set to a fixed value, an error between a true value and the fixed value increases and thus accuracy of measurement of the amount of moisture may deteriorate.

However, the measurement device 100 receives a reflected wave and calculates a reciprocating delay time from a reflection coefficient. Accordingly, even when the reciprocating delay time varies due to temperature change, the measurement device 100 can acquire the value when the reciprocating delay time varies. Accordingly, it is possible to improve accuracy of measurement of the amount of moisture as compared to a case in which the reciprocating delay time is set to a fixed time.

[Operation Example of Measurement Device]

Figure 17:
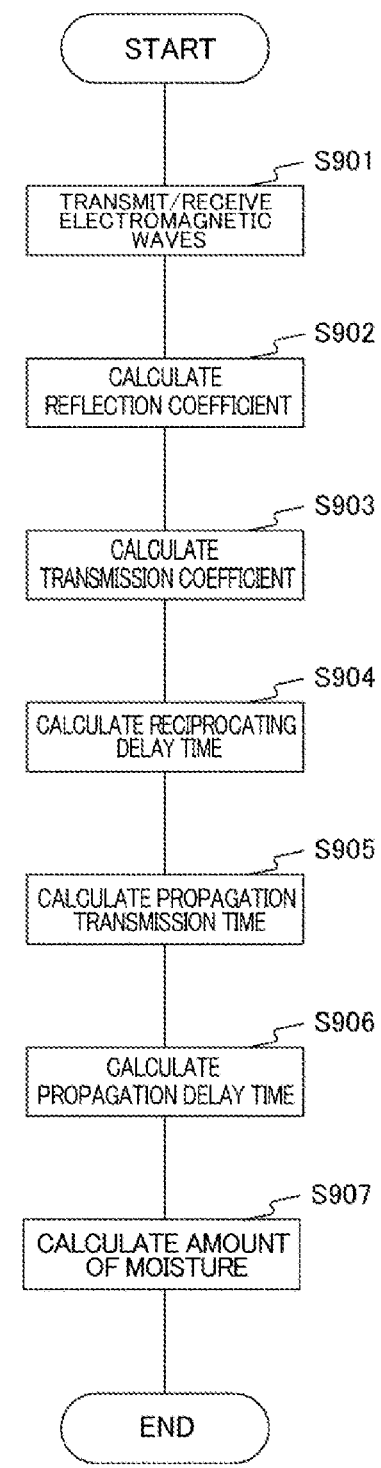
FIG. 17 is a flowchart illustrating an example of operation of the measurement device in the first embodiment of the present technology.

FIG. 17 is a flowchart illustrating an example of operation of the measurement device 100 in the first embodiment of the present technology. The operation in the figure starts, for example, when a predetermined application for measuring an amount of moisture has been executed.

The pair of probes 201 and 202 transmits and receives electromagnetic waves (step S901). The measurement unit 300 calculates a reflection coefficient from an incident wave and a reflected wave (step S902) and calculates a transmission coefficient from the incident wave and a transmitted wave (step S903).

Subsequently, the signal processing unit 400 calculates a reciprocating delay time from the reflection coefficient (step S904) and calculates a propagation transmission time from the transmission coefficient (step S905). The signal processing unit 400 calculates a propagation delay time from the reciprocating delay time and the propagation transmission time (step S906) and calculates an amount of moisture from the propagation delay time and coefficients a and b (step S907). After step S907, the measurement device 100 ends the operation for measurement.

In this manner, according to the first embodiment of the present technology, the measurement device 100 obtains a reciprocating delay time over which an electrical signal reciprocates the cable 308 and measures an amount of moisture from the reciprocating delay time and thus can measure the amount of moisture with high accuracy even when the reciprocating delay time has varied.

2. Second Embodiment

In the above-described first embodiment, the measurement unit 300 and the signal processing unit 400 are mounted in different semiconductor chips. In this configuration, however, it is necessary to provide an interface for communication between the semiconductor chips and thus the circuit scale of the measurement device 100 may increase. A measurement device 100 of the second embodiment differs from the first embodiment in that functions of the measurement unit 300 and the signal processing unit 400 are realized through a single semiconductor chip.

Figure 18:
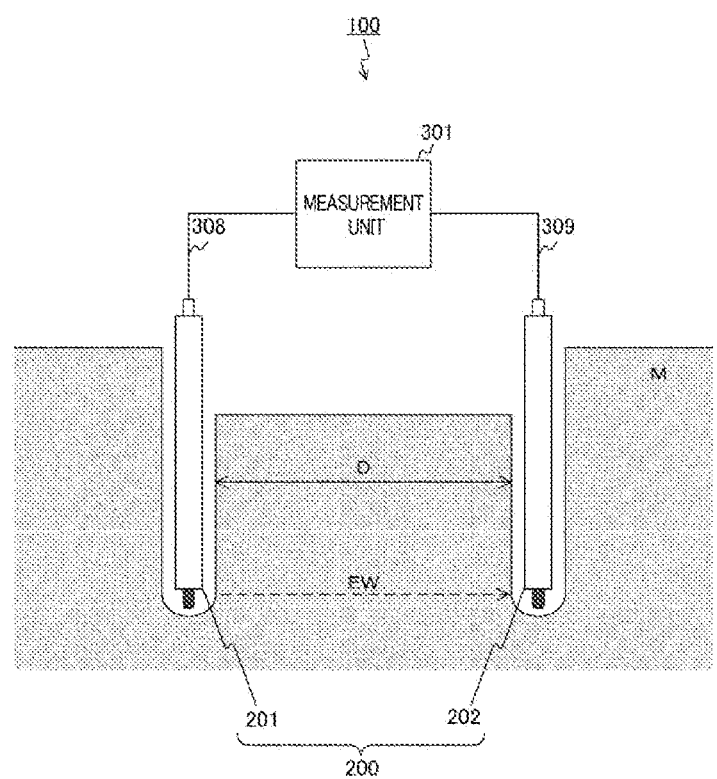
FIG. 18 is a block diagram illustrating a configuration example of a measurement device in a second embodiment of the present technology.

FIG. 18 is a block diagram illustrating a configuration example of the measurement device 100 in the second embodiment of the present technology. The measurement device 100 of the second embodiment differs from the first embodiment in that it includes a measurement unit 301 instead of the measurement unit 300 and the signal processing unit 400.

The measurement unit 301 has the function of the signal processing unit 400 in addition to the function of the measurement unit 300 of the first embodiment.

Figure 19:
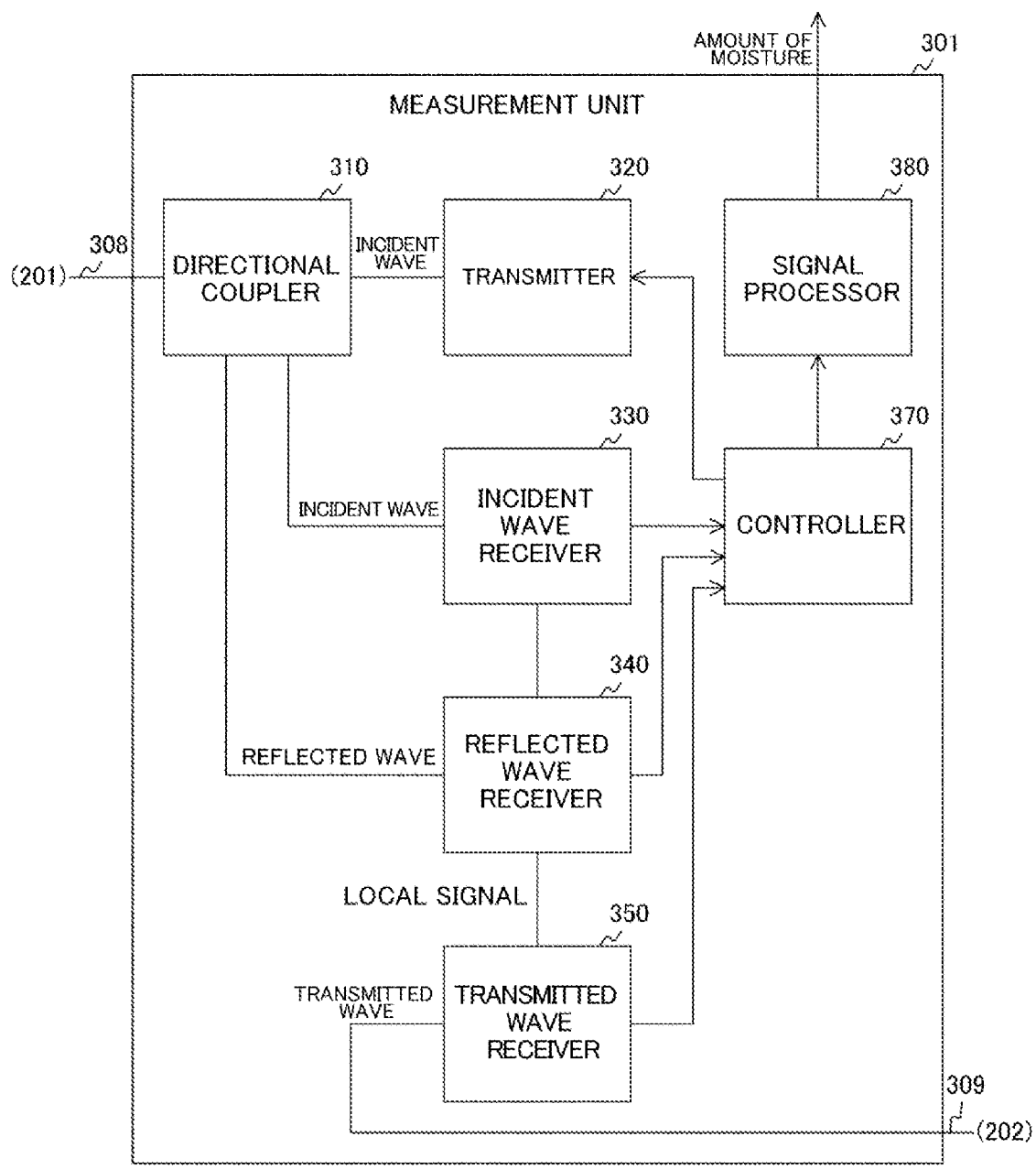
FIG. 19 is a block diagram illustrating a configuration example of a measurement unit in the second embodiment of the present technology.

FIG. 19 is a block diagram illustrating a configuration example of the measurement unit 301 in the second embodiment of the present technology. The measurement unit 301 of the second embodiment differs from the first embodiment in that it includes a signal processor 380 instead of the communication unit 360. The configuration of the signal processor 380 is the same as that of the signal processing unit 400 of the first embodiment. In addition, the function of the controller 370 is realized by, for example, a digital signal processing (DSP) circuit in the figure.

Further, the measurement unit 301 is assumed to be mounted in a single semiconductor chip. Accordingly, it is possible to realize the functions of the measurement unit 300 and the signal processing unit 400 through the single semiconductor chip. Therefore, an interface (the communication unit 360 or the like) for performing communication between semiconductor chips is not necessary and thus the circuit scale of the measurement device 100 can be reduced.

In this manner, according to the second embodiment of the present technology, since the functions of the measurement unit 300 and the signal processing unit 400 are mounted in a single semiconductor chip as described above, the circuit scale of the measurement device 100 can be reduced as compared to a case in which they are mounted in different semiconductor chips.

3. Third Embodiment

Although the measurement unit 300 and the signal processing unit 400 are wired-connected through the signal line 409 in the above-described first embodiment, it is difficult to dispose the signal processing unit 400 at a remote place separated from a measurement point in this configuration. A measurement unit 300 of the third embodiment differs from the first embodiment in that measurement data is wirelessly transmitted.

Figure 20:
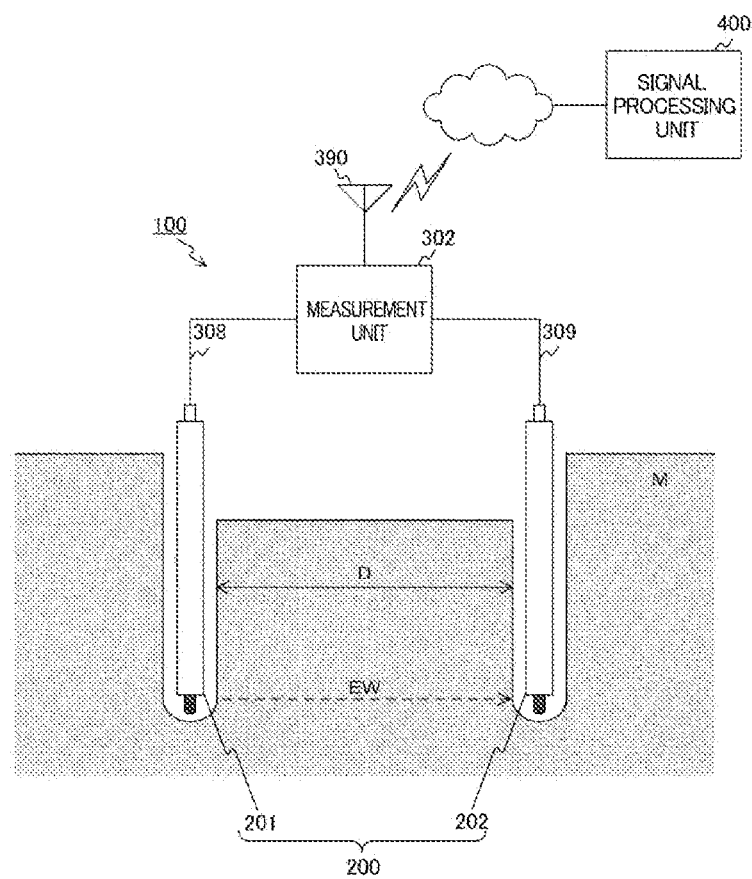
FIG. 20 is a block diagram illustrating a configuration example of a measurement system in a third embodiment of the present technology.

FIG. 20 is a block diagram illustrating a configuration example of a measurement system in the third embodiment of the present technology. The measurement system of the third embodiment includes a sensor device 110 and a signal processing unit 400.

The sensor device 110 of the third embodiment includes a measurement unit 302 instead of the measurement unit 300. A communication unit 360 of the measurement unit 302 differs from the first embodiment in that it wirelessly transmits measurement data to the signal processing unit 400 through an antenna 390.

The signal processing unit 400 is connected to a network of a base station or the Internet and receives the wirelessly transmitted measurement data through the network or the Internet in a wired or wireless manner.

As illustrated in the figure, since the measurement unit 302 and the signal processing unit 400 are wirelessly connected, the signal processing unit 400 can be disposed at a remote place separated from a measurement point.

In this manner, according to the third embodiment of the present technology, the signal processing unit 400 can be disposed at a remote place because the measurement unit 302 wirelessly transmits measurement data to the signal processing unit 400.

4. Fourth Embodiment

In the above-described first embodiment, an amount of moisture is measured on the assumption that delay times over which an electrical signal is transmitted through the cables 308 and 309 are identical. However, when the cables 308 and 309 have different lengths, the delay times have different values and the assumption is violated and thus measurement error may be generated. A measurement device 100 of the fourth embodiment differs from the first embodiment in that both a reciprocating delay time of the cable 308 and a reciprocating delay time of the cable 309 are obtained and an amount of moisture is measured.

Figure 21:
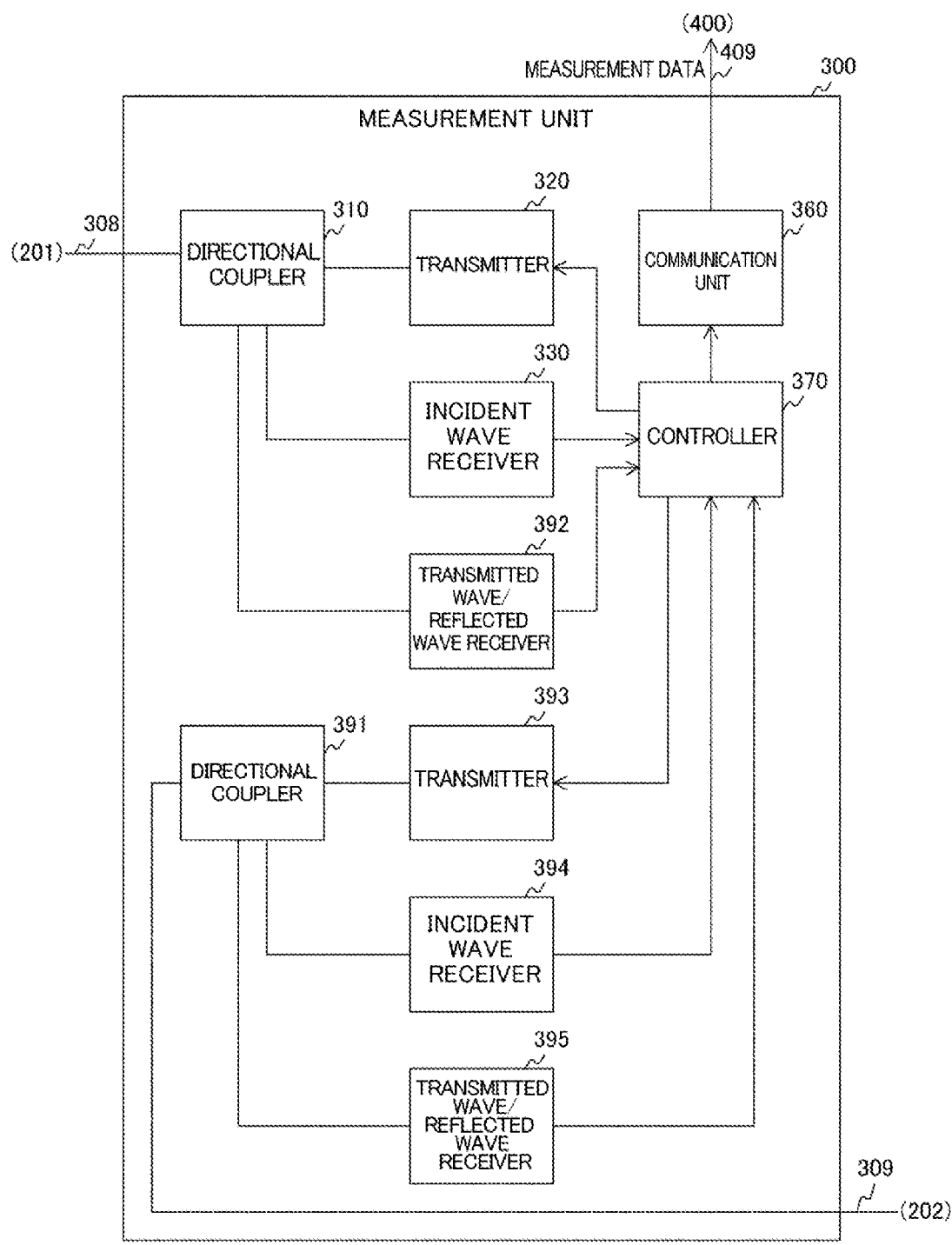
FIG. 21 is a block diagram illustrating a configuration example of a measurement unit in a fourth embodiment of the present technology.

FIG. 21 is a block diagram illustrating a configuration example of a measurement unit 300 in the fourth embodiment of the present technology. The measurement unit 300 of the fourth embodiment includes directional couplers 310 and 391, transmitters 320 and 393, incident wave receivers 330 and 394, transmitted wave/reflected wave receivers 392 and 395, a communication unit 360, and a controller 370.

The transmitter 320 transmits an incident wave I1 through the cable 308. The transmitter 393 transmits an incident wave I2 through the cable 309. The controller 370 controls the transmitters 320 and 393 to cause them to sequentially transmit the incident waves I1 and I2.

The incident wave receiver 330 receives the incident wave I1 when the incident wave I1 has been transmitted. The incident wave receiver 394 receives the incident wave I2 when the incident wave I2 has been transmitted.

The directional coupler 310 separates an electrical signal of the cable 308 into an incident wave and a reflected wave. When the incident wave I1 has been transmitted, the directional coupler 310 separates the electrical signal of the cable 308 into the incident wave I1 and a reflected wave R1 corresponding to the incident wave I1. On the other hand, when the incident wave I2 has been transmitted, the directional coupler 310 outputs a transmitted wave Tr1 corresponding to the incident wave I2.

The directional coupler 391 separates an electrical signal of the cable 309 into an incident wave and a reflected wave. When the incident wave I2 has been transmitted, the directional coupler 391 separates the electrical signal of the cable 308 into the incident wave I2 and a reflected wave R2 corresponding to the incident wave I2. On the other hand, when the incident wave I1 has been transmitted, the directional coupler 391 outputs a transmitted wave Tr2 corresponding to the incident wave I1.

The transmitted wave/reflected wave receiver 392 sequentially receives a transmitted wave and a reflected wave. The transmitted wave/reflected wave receiver 392 receives the reflected wave R1 from the directional coupler 310 when the incident wave I1 has been transmitted and receives the transmitted wave Tr1 from the directional coupler 310 when the incident wave I2 has been transmitted.

The transmitted wave/reflected wave receiver 395 sequentially receives a transmitted wave and a reflected wave. The transmitted wave/reflected wave receiver 395 receives the transmitted wave Tr2 from the directional coupler 391 when the incident wave I1 has been transmitted and receives the reflected wave R2 from the directional coupler 391 when the incident wave I2 has been transmitted.

Meanwhile, the incident waves I1 and I2 are an example of first and second incident waves in the claims and the reflected waves R1 and R2 are an example of first and second reflected waves in the claims. The transmitted waves Tr1 and Tr2 are an example of first and second transmitted waves in the claims. In addition, the directional couplers 310 and 391 are an example of first and second directional couplers in the claims and the transmitters 320 and 393 are an example of first and second transmitters in the claims. The transmitted wave/reflected wave receivers 392 and 395 are an example of first and second receivers in the claims.

The controller 370 calculates a reflection coefficient $\Gamma_{11}$ from complex amplitudes of the incident wave I1 and the reflected wave R1 and calculates a transmission coefficient $T_{21}$ from complex amplitudes of the incident wave I1 and the transmitted wave Tr2 through the same method as that of the first embodiment. In addition, the controller 370 calculates a reflection coefficient $\Gamma_{22}$ from complex amplitudes of the incident wave I2 and the reflected wave R2 and calculates a transmission coefficient $T_{12}$ from complex amplitudes of the incident wave I2 and the transmitted wave Tr1 through the same method as that of the first embodiment.

The signal processing unit 400 in the subsequent stage calculates a reciprocating delay time $\tau_{11}$ and a propagation transmission time $\tau_{12}$ from the reflection coefficient $\Gamma_{11}$ and the transmission coefficient $T_{12}$ through the same method as that of the first embodiment. In addition, the signal processing unit 400 calculates a reciprocating delay time $\tau_{22}$ and a propagation transmission time $\tau_{21}$ from the reflection coefficient $\Gamma_{22}$ and the transmission coefficient $T_{12}$ through the same method as that of the first embodiment.

Then, the signal processing unit 400 calculates a propagation delay time $\tau_d$ according to the following formula.

$$\tau_d = (\tau_{21} + \tau_{12} - \tau_{11} - \tau_{22})/2 \qquad \text{Formula 5}$$

Subsequently, the signal processing unit 400 measures an amount of moisture by putting the propagation delay time $\tau_d$ calculated according to Formula 5 into Formula 4. Meanwhile, the reciprocating delay times $\tau_{11}$ and $\tau_{22}$ are an example of first and second reciprocating delay times in the claims.

When the cables 308 and 309 have different lengths, delay times over which an electrical signal is transmitted through the respective cables may be different from each other. Even in this case, however, a measurement error caused by a difference between the lengths of the cables 308 and 309 can be reduced by performing arithmetic operations using the reciprocating delay time $\tau_{22}$ in addition to the reciprocating delay time $\tau_{11}$ according to Formula 5.

Meanwhile, the second embodiment or the third embodiment can be applied to the fourth embodiment.

In this manner, according to the fourth embodiment of the present technology, since an amount of moisture is measured using the reciprocating delay time $\tau_{11}$ corresponding to the cable 308 and the reciprocating delay time $\tau_{22}$ corresponding to the cable 309, a measurement error caused by a difference between the lengths of the cables can be reduced.

Meanwhile, the above-described embodiments represent an example for embodying the present technology, and there is a corresponding relationship between matters in the embodiments and matters used to define the invention in the claims. Likewise, there is a corresponding relationship between matters used to define the invention in the claims and matters in the same names in the embodiments of the present technology. However, the present technology is not limited to the embodiments and can be embodied by modifying the embodiments in various manners without departing from the gist of the present technology.

In addition, the processing procedure described in the above-described embodiments may be taken as a method having the procedure or taken as a program for causing a computer to execute the procedure or a recording medium storing the program. As this recording medium, for example, a compact disc (CD), a minidisc (MD), a digital versatile disc (DVD), a memory card, a Blu-ray (registered trademark) disc, or the like can be used.

Meanwhile, the advantageous effects described in the present specification are merely exemplary and are not intended as limiting, and other advantageous effects may be obtained.

Meanwhile, the present technology can employ the following configurations.

(1) A measurement device including:
a transmitter configured to transmit an electrical signal including an incident wave to one of a pair of probes in which a cable has been embedded through the cable; a receiver configured to receive a reflected wave obtained from reflection of the incident wave by the one of the pair of probes and a transmitted wave that has been transmitted through a medium between the pair of probes through the cable; and a processing unit configured to obtain a reciprocating delay time corresponding to a time over which the electrical signal reciprocates through the cable and to measure an amount of moisture contained in the medium on the basis of the reciprocating delay time and a propagation transmission time corresponding to a time over which electromagnetic waves propagate and the electrical signal is transmitted through the medium and the cable.

(2) The measurement device according to (1), further including an outer shell configured to isolate the pair of probes from the medium.

(3) The measurement device according to (2), wherein the outer shell is formed of an electromagnetic wave transmitting material.

(4) The measurement device according to (3), further including a spacer configured to keep a constant interval between the pair of probes.

(5) The measurement device according to (4), wherein the spacer is formed of an electromagnetic wave transmitting material.

(6) The measurement device according to (5), wherein an outer edge of the spacer which is close to antenna parts of the pair of probes between outer edges extending between the pair of probes has an arc shape.

(7) The measurement device according to (6), wherein a distance from the antenna parts of the pair of probes to a lower end of the spacer is greater than an inter-antenna distance corresponding to a distance between the antenna parts, desirably, greater than twice the inter antenna distance, more desirably, greater than three times the inter-antenna distance, and less than a length of the probes.

(8) The measurement device according to any one of (1) to (7), further including a controller configured to perform control for causing the incident wave to be transmitted, processing of obtaining a ratio between complex amplitudes of the incident wave and the reflected wave as a reflection coefficient, and processing of obtaining a ratio between complex amplitudes of the incident wave and the transmitted wave as a transmission coefficient, wherein the processing unit obtains the reciprocating delay time and the propagation transmission time on the basis of the reflection coefficient and the transmission coefficient.

(9) The measurement device according to any one of (1) to (8), wherein the controller and the processing unit are provided in a predetermined semiconductor chip.

(10) The measurement device according to (8), wherein the controller is a provided in a predetermined semiconductor chip, and the processing unit is provided in a semiconductor chip different from the semiconductor chip.

(11) The measurement device according to (8), further including a communication unit configured to wirelessly transmit the reflection coefficient and the transmission coefficient to the processing unit.

(12) The measurement device according to any one of (8) to (11), further including a directional coupler configured to separate an electrical signal transmitted through the cable into the incident wave and the reflected wave.

(13) The measurement device according to (12), wherein the receiver includes an incident wave receiver configured to receive the incident wave, a reflected wave receiver configured to receive the reflected wave, and a transmitted wave receiver configured to receive the transmitted wave.

(14) The measurement device according to (12), wherein the incident wave includes first and second incident waves in different directions, the reflected wave includes a first reflected wave corresponding to the first incident wave and a second reflected wave corresponding to the second incident wave, the transmitted wave includes a second transmitted wave corresponding to the first incident wave and a first transmitted wave corresponding to the second incident wave, the directional coupler includes a first directional coupler configured to separate the electrical signal into the first incident wave and the first reflected wave and a second directional coupler configured to separate the electrical signal into the second incident wave and the second reflected wave, the transmitter includes a first transmitter configured to transmit the first incident wave and a second transmitter configured to transmit the second incident wave, and the receiver includes a first receiver configured to sequentially receive the first reflected wave and the first transmitted wave and a second receiver configured to sequentially receive the second reflected wave and the second transmitted wave.

(15) The measurement device according to (14), wherein the reciprocating delay time includes a first reciprocating delay time corresponding to one of the pair of probes and a second reciprocating delay time corresponding to the other of the pair of probes, and the processing unit obtains the first reciprocating delay time from the first incident wave and the first reflected wave and obtains the second reciprocating delay time from the second incident wave and the second reflected wave.

(16) The measurement device according to any one of (1) to (15), wherein the processing unit obtains a propagation delay time corresponding to a time over which the electromagnetic waves propagate through the medium from the reciprocating delay time and the propagation transmission time and measures an amount of moisture according to the propagation delay time.

(17) The measurement device according to (16), wherein the processing unit stores a predetermined coefficient representing a relationship between the propagation delay time and the amount of moisture and measures the amount of moisture from the obtained propagation delay time and the coefficient.

(18) A measurement system including:

a transmitter configured to transmit an electrical signal including an incident wave to one of a pair of probes to which a cable has been connected through the cable;

a receiver configured to receive a reflected wave obtained from reflection of the incident wave by the one of the pair of probes and a transmitted wave that has been transmitted through a medium between the pair of probes through the cable; and a controller configured to perform control for causing the incident wave to be transmitted and processing of obtaining a ratio between complex amplitudes of the incident wave and the reflected wave as a reflection coefficient; and a processing unit configured to obtain a reciprocating delay time corresponding to a time over which the electrical signal reciprocates through the cable from the reflection coefficient and to measure an amount of moisture contained in the medium on the basis of the reciprocating delay time and a propagation transmission time corresponding to a time over which electromagnetic waves propagate and the electrical signal is transmitted through the medium and the cable.

(19) A measurement method including:

a transmission procedure of transmitting an electrical signal including an incident wave to one of a pair of probes in which a cable has been embedded through the cable;

a reception procedure of receiving a reflected wave obtained from reflection of the incident wave by the one of the pair of probes and a transmitted wave that has been transmitted through a medium between the pair of probes through the cable; and a processing procedure of obtaining a reciprocating delay time corresponding to a time over which the electrical signal reciprocates through the cable and measuring an amount of moisture contained in the medium on the basis of the reciprocating delay time and a propagation transmission time corresponding to a time over which electromagnetic waves propagate and the electrical signal is transmitted through the medium and the cable.

REFERENCE SIGNS LIST

100 Measurement device
110 Sensor device
200 Sensor head
201, 202 Probe
210 Antenna part
211 Core wire part
212 Shield part
213 Electrode part
225 Outer shell
240 Electromagnetic wave absorbing material
260 Spacer
300, 301, 302 Measurement unit
308, 309 Cable
310, 391 Directional coupler
311, 312, 313 Transmission line
314, 315 Terminating resistor
320, 393 Transmitter
321 Driver
322 Transmission signal oscillator
330, 394 Incident wave receiver
331, 341, 353 Mixer
332, 342, 354 Band pass filter
333, 343, 355 Analog-to-digital converter
340 Reflected wave receiver
350 Transmitted wave receiver
351 Receiver
352 Local signal oscillator
360, 410 Communication unit
370 Controller
371 Transmission controller
372 Reflection coefficient calculation unit
373 Transmission coefficient calculation unit
380 Signal processor
390 Antenna
392, 395 Transmitted wave/reflected wave receiver
400 Signal processing unit
420 Reciprocating delay time calculation unit
430 Propagation transmission time calculation unit
440 Moisture amount measurement unit
450 Coefficient storing unit

What is claimed is:

1. A measurement device comprising:
a transmitter configured to transmit an electrical signal including an incident wave to a cable embedded in a first probe of a pair of probes, wherein the cable is also embedded in a second probe of the pair of probes;
a receiver configured to receive:
a reflected wave obtained from a reflection of the incident wave that traveled through the cable in the first probe of the pair of probes; and
a transmitted wave that has been transmitted through a medium between the pair of probes to the cable in the second probe of the pair of probes; and
a signal processor configured to:
obtain a reciprocating delay time based on the reflected wave, the reciprocating delay time corresponding to a time taken for the incident wave to travel to an end of the first probe and reflect back to the receiver as the reflected wave;
obtain a propagation transmission time based on the transmitted wave, the propagation transmission time corresponding to a time taken for electromagnetic waves generated by the incident wave that traveled through the cable in the first probe to propagate through the medium and return to the receiver through the cable in the second probe as the transmitted wave; and
measure an amount of moisture contained in the medium based on the reciprocating delay time and the propagation transmission time; and
a controller configured to perform:
processing to obtain a ratio between complex amplitudes of the incident wave and the reflected wave as a reflection coefficient,
wherein the signal processor obtains the reciprocating delay time based on the reflection coefficient.

2. The measurement device according to claim 1, further comprising an outer shell configured to isolate the pair of probes from the medium.

3. The measurement device according to claim 2, wherein the outer shell is formed of an electromagnetic wave transmitting material.

4. The measurement device according to claim 3, further comprising a spacer configured to keep a constant interval between the pair of probes.

5. The measurement device according to claim 4, wherein the spacer is formed of an electromagnetic wave transmitting material.

6. The measurement device according to claim 5, wherein each of the first probe and the second probe includes an antenna part, and wherein an outer edge of the spacer that is closer to the antenna parts of the pair of probes has an arc shape.

7. The measurement device according to claim 6, wherein a distance from the antenna parts of the pair of probes to a lower end of the spacer is i) greater than an inter-antenna distance corresponding to a distance between the antenna parts, and ii) less than a length of the probes.

8. The measurement device according to claim 1, wherein the controller is configured to perform:
control for causing the incident wave to be transmitted; and
processing to obtain a ratio between complex amplitudes of the incident wave and the transmitted wave as a transmission coefficient,
wherein the signal processor obtains the propagation transmission time on the basis of the transmission coefficient.

9. The measurement device according to claim 8, wherein the controller and the signal processor are provided in a semiconductor chip.

10. The measurement device according to claim 8, wherein the controller is provided in a first semiconductor chip, and
the signal processor is provided in a second semiconductor chip different from the first semiconductor chip.

11. The measurement device according to claim 8, further comprising a communication interface configured to wirelessly transmit the reflection coefficient and the transmission coefficient to the signal processor.

12. The measurement device according to claim 8, further comprising a directional coupler configured to separate the incident wave and the reflected wave.

13. The measurement device according to claim 12, wherein the receiver includes:

an incident wave receiver configured to receive the incident wave;
a reflected wave receiver configured to receive the reflected wave; and
a transmitted wave receiver configured to receive the transmitted wave.

14. The measurement device according to claim 12, wherein the incident wave includes first and second incident waves in different directions,
wherein the reflected wave includes a first reflected wave corresponding to the first incident wave and a second reflected wave corresponding to the second incident wave,
wherein the transmitted wave includes a second transmitted wave corresponding to the first incident wave and a first transmitted wave corresponding to the second incident wave,
wherein the directional coupler includes a first directional coupler configured to separate the electrical signal into the first incident wave and the first reflected wave, and a second directional coupler configured to separate the electrical signal into the second incident wave and the second reflected wave,
wherein the transmitter includes a first transmitter configured to transmit the first incident wave and a second transmitter configured to transmit the second incident wave, and
wherein the receiver includes a first receiver configured to sequentially receive the first reflected wave and the first transmitted wave and a second receiver configured to sequentially receive the second reflected wave and the second transmitted wave.

15. The measurement device according to claim 14, wherein the reciprocating delay time includes a first reciprocating delay time corresponding to one of the pair of probes and a second reciprocating delay time corresponding to the other of the pair of probes, and
the signal processor obtains the first reciprocating delay time from the first incident wave and the first reflected wave and obtains the second reciprocating delay time from the second incident wave and the second reflected wave.

16. The measurement device according to claim 1, wherein the signal processor obtains a propagation delay time, corresponding to a time over which the electromagnetic waves propagate through the medium, from the reciprocating delay time and the propagation transmission time, and measures an amount of moisture according to the propagation delay time.

17. The measurement device according to claim 16, wherein the signal processor stores a coefficient representing a relationship between the propagation delay time and the amount of moisture and measures the amount of moisture from the obtained propagation delay time and the coefficient.

18. A measurement system comprising:
a transmitter configured to transmit an electrical signal including an incident wave to a cable embedded in a first probe of a pair of probes, wherein the cable is also embedded in a second probe of the pair of probes;
a receiver configured to receive:
a reflected wave obtained from a reflection of the incident wave that traveled through the cable in the first probe of the pair of probes; and
a transmitted wave that has been transmitted through a medium between the pair of probes to the cable in the second probe of the pair of probes;
a controller configured to perform:
control for causing the incident wave to be transmitted; and
processing to obtain a ratio between complex amplitudes of the incident wave and the reflected wave as a reflection coefficient; and
a signal processor configured to:
obtain a reciprocating delay time based on the reflection coefficient, the reciprocating delay time corresponding to a time taken for the incident wave to travel to an end of the first probe and reflect back to the receiver as the reflected wave;
obtain a propagation transmission time based on the transmitted wave, the propagation transmission time corresponding to a time taken for electromagnetic waves generated by the incident wave that traveled through the cable in the first probe to propagate through the medium and return to the receiver through the cable in the second probe as the transmitted wave; and
measure an amount of moisture contained in the medium based on the reciprocating delay time and the propagation transmission time.

19. A measurement method comprising:
transmitting an electrical signal including an incident wave to a first probe of a pair of probes in which a cable has been embedded, wherein the cable is also embedded in a second probe of the pair of probes;
receiving a reflected wave obtained from a reflection of the incident wave that traveled through the cable in the first probe of the pair of probes;
receiving a transmitted wave that has been transmitted through a medium between the pair of probes to the cable in the second probe of the pair of probes;
processing to obtain a ratio between complex amplitudes of the incident wave and the reflected wave as a reflection coefficient;
obtaining a reciprocating delay time based on the reflection coefficient, the reciprocating delay time corresponding to a time taken for the incident wave to travel to an end of the first probe and reflect back to the receiver as the reflected wave;
obtaining a propagation transmission time based on the transmitted wave, the propagation transmission time corresponding to a time taken for electromagnetic waves generated by the incident wave that traveled through the cable in the first probe to propagate through the medium and return to the receiver through the cable in the second probe as the transmitted wave; and
measuring an amount of moisture contained in the medium based on the reciprocating delay time and the propagation transmission time.

* * * * *